(12) United States Patent
Russell et al.

(10) Patent No.: US 8,227,603 B2
(45) Date of Patent: Jul. 24, 2012

(54) MODULATING SKELETAL MUSCLE

(75) Inventors: Alan Russell, San Francisco, CA (US); Fady Malik, Burlingame, CA (US); Jim Hartman, San Francisco, CA (US); Richard Hansen, San Carlos, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 983 days.

(21) Appl. No.: 12/165,498

(22) Filed: Jun. 30, 2008

(65) Prior Publication Data

US 2009/0029345 A1    Jan. 29, 2009

Related U.S. Application Data

(63) Continuation-in-part of application No. 11/888,902, filed on Aug. 1, 2007, now Pat. No. 7,598,248, and a continuation-in-part of application No. PCT/US2007/017191, filed on Jul. 31, 2007.

(60) Provisional application No. 60/835,272, filed on Aug. 2, 2006, provisional application No. 60/921,054, filed on Mar. 30, 2007, provisional application No. 60/834,906, filed on Aug. 1, 2006, provisional application No. 60/836,747, filed on Aug. 9, 2006, provisional application No. 60/920,921, filed on Mar. 30, 2007.

(51) Int. Cl.
    *C07D 471/00* (2006.01)
(52) U.S. Cl. .............................. 544/350; 435/375; 435/4
(58) Field of Classification Search .............. 435/4, 375; 544/350

See application file for complete search history.

(56) References Cited

U.S. PATENT DOCUMENTS

| | | | |
|---|---|---|---|
| 3,507,866 A | 4/1970 | Jones et al. | |
| 4,195,088 A | 3/1980 | Barzaghi et al. | |
| 4,943,573 A | 7/1990 | Meanwell | |
| 5,354,759 A | 10/1994 | Oku et al. | |
| 6,162,804 A | 12/2000 | Bilodeau et al. | |
| 6,232,320 B1 | 5/2001 | Stewart et al. | |
| 6,579,882 B2 | 6/2003 | Stewart et al. | |
| 6,638,933 B2 | 10/2003 | Gerlach et al. | |
| 6,657,064 B2 | 12/2003 | Gerlach et al. | |
| 7,279,580 B2 | 10/2007 | Goodacre et al. | |
| 7,348,339 B2 | 3/2008 | Bailey et al. | |
| 7,598,248 B2 | 10/2009 | Muci et al. | |
| 7,851,484 B2 | 12/2010 | Morgan et al. | |
| 2003/0220365 A1 | 11/2003 | Stewart et al. | |
| 2004/0023972 A1 | 2/2004 | Sundermann et al. | |
| 2004/0166137 A1 | 8/2004 | Lackey | |
| 2005/0197328 A1 | 9/2005 | Bailey et al. | |
| 2005/0250794 A1 | 11/2005 | Napper et al. | |
| 2006/0019952 A1 | 1/2006 | Distefano et al. | |
| 2006/0148805 A1 | 7/2006 | Chen et al. | |
| 2007/0197507 A1 | 8/2007 | Morgan et al. | |
| 2007/0275984 A1 | 11/2007 | Imogai et al. | |
| 2008/0096903 A1 | 4/2008 | Chen et al. | |
| 2008/0146561 A1 | 6/2008 | Muci et al. | |
| 2008/0242695 A1 | 10/2008 | Morgan et al. | |
| 2009/0023724 A1 | 1/2009 | Mortensen et al. | |
| 2009/0029345 A1 | 1/2009 | Russell et al. | |
| 2009/0082370 A1 | 3/2009 | Thompson et al. | |
| 2009/0247538 A1 | 10/2009 | Berdini et al. | |
| 2009/0247571 A1 | 10/2009 | Muci et al. | |
| 2010/0022564 A1 | 1/2010 | Davies et al. | |

FOREIGN PATENT DOCUMENTS

| | | |
|---|---|---|
| DE | 2241575 | 3/1973 |
| GB | 2174987 A | 11/1986 |
| GB | 2190676 A | 11/1987 |
| GB | 2400101 A | 6/2004 |
| IL | 40080 A | 12/1975 |
| JP | 06-041135 A | 2/1994 |
| WO | WO 99/62908 A2 | 12/1999 |
| WO | WO 2004/092166 A2 | 10/2004 |
| WO | WO 2005/002520 A3 | 1/2005 |
| WO | WO 2005/013894 A2 | 2/2005 |
| WO | WO 2005/060711 A2 | 7/2005 |
| WO | WO 2005/072412 A2 | 8/2005 |
| WO | WO 2005/108374 A1 | 11/2005 |
| WO | WO 2006/030031 A1 | 3/2006 |
| WO | WO 2006/036883 A2 | 4/2006 |
| WO | WO 2006/046024 A1 | 5/2006 |
| WO | WO 2006/088836 A2 | 8/2006 |
| WO | WO 2007/125310 A2 | 11/2007 |
| WO | WO 2007/125321 A2 | 11/2007 |
| WO | WO 2008/016648 A2 | 2/2008 |
| WO | WO 2008/049105 A2 | 4/2008 |
| WO | WO 2008/051493 A2 | 5/2008 |
| WO | WO 2008/075007 A1 | 6/2008 |
| WO | WO 2008/089459 A1 | 7/2008 |
| WO | WO 2010/068483 A2 | 6/2010 |

OTHER PUBLICATIONS

Morimoto et al "Ca2+ binding to skeletal muscle troponic C in skeletal and cardiac myofibrils", J. biochem., 105, 435-439 (1989).*
Restriction Requirement for U.S. Appl. No. 12/765,820 mailed Apr. 22, 2010.
Restriction Requirement for U.S. Appl. No. 12/780,644 mailed Jan. 6, 2012.
Advisory Action for U.S. Appl. No. 12/573,730 mailed Dec. 21, 2010.
Barlin Aust. J. Chem., 25.2299-2306 (1982).
Bianchi et al., Compounds with Antiulcer and antisecretory activity. III. N-substituted imidazolones condensed with nitrogen-containing heteroaromatic rings, European Journal of Medical Chemistry (1983), 18(6), 501-6.
Bjoerk et al., Synthesis of Novel 2-Aminoimidazo [4,5-b] Pyridines, Including the Thieno Analogue of the Cooked-Food Mutagen IFP, Journal of Heterocyclic Chemistry, 43(1): 101-109 (2006).
Bonnet et al: "Synthesis and antibronchospastic activity of 8-alkoxy- and 8-(alkylamino)imidazo(1,2-a)pyrazines" Journal of Medicinal Chemistry, vol. 35, No. 18, Jan. 1, 1992, pp. 3353-3358.

(Continued)

*Primary Examiner* — Brandon Fetterolf
*Assistant Examiner* — Jean Cornet
(74) *Attorney, Agent, or Firm* — Foley & Lardner LLP

(57) ABSTRACT

Methods of identifying skeletal muscle activators are provided. Methods of activating skeletal muscle using skeletal muscle activators are also provided.

21 Claims, 6 Drawing Sheets

OTHER PUBLICATIONS

Dorwald, Side Reactions in Organic Synthesis: A Guide to Successful Synthesis Design, Weinheim: Wiley-VCH Verlag GmbH & Co., KGaA, Preface (2005).
International Search Report and Written Opinion mailed Jul. 1, 2008 for PCT/US2008/004075.
International Search Report and Written Opinion mailed Aug. 8, 2008 for PCT/US2007/017191.
International Search Report and Written Opinion mailed Oct. 1, 2008 for PCT/US2007/017235.
International Search Report and Written Opinion mailed Apr. 8, 2009 for PCT/US2009/000686.
Jordan, Nature Reviews, Drug Discovery 2:205-213 (Mar. 2003).
Li et al., Skeletal Muscle Respiratory Uncoupling Prevents Diet-Induced Obesity and Insulin Resistance in Mice, Nature Medicine, vol. 6(10), (2000), pp. 115-1120.
Lima et al., Current Medicinal Chemistry 12(1):23-49 (2005).
Lindstroem et al., Synthesis of the Mutagenic 2-Amino-1,6-Dimethyl-Imidazo[4,5-b]Pyridine (1,6-DMIP) and Five of Its Isomers, Heterocycles, Elsevier Science Publishers B.V. (1994), 38(3), 529-40.
Meanwell et al., 1,3 Dihydro-2H-Imidazo[4,5-b]quinolin-2-ones—Inhibitors of Blood Platelet cAMP Phosphodiesterase and Induced Aggregation Journal of Medicinal Chemistry (1991), 34(9), 2906-16.
Meanwell et al., Inhibitors of Blood Platelet cAMP Phosphodiesterase.2. Structure-activity Relationships Associated with 1,3-dihydro-2H-imidazo[4,5-b]quinolin-2-ones substituted with functionalized side chains, Journal of Medicinal Chemistry, 35(14):2672-87 (1992).
Meanwell et al., Inhibitors of Blood Platelet cAMP Phosphodiesterase. 3. 1,3-Dihydro-2H-imidazo[4,5-b]quinolin-2-one derivates with enhanced aqueous solubility, Journal of Medicinal Chemistry, 35(14): 2688-96 (1992).
Niel et al., Sexual Differentiation of the Spinal Nucleus of the Bulbocavernosus is not Medicated Solely by Adrogen Receptors in Muscle Fibers, Endocrinology, (2009), 150(7), pp. 3207-3213.
Notice of Allowance for U.S. Appl. No. 11/888,902 mailed Jun. 1, 2009.
Notice of Allowance for U.S. Appl. No. 12/058,127 mailed Aug. 9, 2010.
Notice of Allowance for U.S. Appl. No. 12/573,730 mailed Feb. 1, 2011.
Notice of Allowance for U.S. Appl. No. 12/364,394 mailed Mar. 22, 2011.
Notice of Allowance for U.S. Appl. No. 12/359,186 mailed Apr. 11, 2011.
Notice of Allowance for U.S. Appl. No. 12/058,127 mailed Nov. 10, 2010.
Office Action for U.S. Appl. No. 11/888,902 mailed Oct. 21, 2008.
Office Action for U.S. Appl. No. 11/888,902 mailed Mar. 5, 2009.
Office Action for U.S. Appl. No. 12/058,127 mailed Feb. 25, 2010.
Office Action for U.S. Appl. No. 12/573,730 mailed Oct. 13, 2010.
Office Action for U.S. Appl. No. 12/573,730 mailed Jul. 8, 2010.
Office Action for U.S. Appl. No. 12/359,186 mailed Dec. 2, 2010.
Restriction Requirement for U.S. Appl. No. 12/573,730 mailed Apr. 29, 2010.
Restriction Requirement for U.S. Appl. No. 12/364,394 mailed Jan. 5, 2011.
Restriction Requirement for U.S. Appl. No. 12/359,186 mailed Sep. 14, 2010.
Restriction Requirement for U.S. Appl. No. 12/058,127 mailed Nov. 23, 2009.
Shirai et al,, "New syntheses and spectral properties of pteridine-related heterocycles from 2,5-diamino-3,6-dicyanopyridine" Journal of Heterocyclic Chemistry, vol. 37, 2000, pp. 1151-1156.
Supplementary European Search Report for EPO Application No. 08742350.5 mailed Apr. 8, 2010.
Vitse et al: "New Imidazo(1,2-a)pyrazine Derivatives with Bronchodilatory and Cyclic Nucleotide Phosphodiesterase Inhibitory Activities" Bioorganic & Medicinal Chemistry, vol. 7, Jan. 1, 1999, pp. 1059-1065.
Yutilov et al., Halogenation of 2-Unsubstituted and 2-Methylimidazo[4,5-b]Pyridine Derivatives, Russian Journal of Organic Chemistry (2005), 41(3), 450-454.
Yutilov et al., Halogenation of Imidazo[4,5-b]Pyridin-2-one Derivatives, Russian Journal of Organic Chemistry (2005), 41(4), 575-579.
Zhu et al., "Synthesis of inidazo[4,5-b]quinoxaline Ribonucleosides as Linear Dimensional Analogs of Antiviral Polyhalogenated Benzimidazole Ribonucleosides" Journal of the Chinese Chemical Society, Chinese Electronic Periodical Services, China, vol. 45, No. 4, pp. 465-474, 1998.
IUPAC Ed. Alan D. McNaught and Andrew Wilkinson "cycloalkyl groups" [Online] Jan. 1, 1997, Compendium of Chemical Terminology: IUPAC Recommendations; [IUPAC Chemical Data Series], Blackwell Science, Oxford [U.A.], XP002585006 ISBN: 978-0-86542-684-9 Retrieved from the Internet: URL: http://www.iupac.org/goldbook/C01498.pdf.
IUPAC Ed—Alan D McNaught and Andrew Wilkinson: "alkyl groups" [Online] Jan. 1, 1997, Compendium of Chemical Terminology: IUPAC Recommendations; [IUPAC Chemical Data Series], Blackwell Science, Oxford [U.A.], XP002585005 ISBN: 978-0-86542-684-9 Retrieved from the Internet: URL:http://www.iupac.org/goldbook/A00228.pdf.

* cited by examiner

MODULATING SKELETAL MUSCLE

The present application is a continuation-in-part of U.S. application Ser. No. 11/888,902, filed Aug. 1, 2007 now U.S. Pat. No. 7,598,248; which claims the benefit of priority to U.S. Provisional Application No. 60/835,272, filed Aug. 2, 2006, and U.S. Provisional Application No. 60/921,054, filed Mar. 30, 2007. This application also is a continuation-in-part of International Application No. PCT/US07/17191, filed Jul. 31, 2007; which claims the benefit of priority to U.S. Provisional Application No. 60/834,906, filed Aug. 1, 2006, U.S. Provisional Application No. 60/836,747, filed Aug. 9, 2006, and U.S. Provisional Application No. 60/920,921, filed Mar. 30, 2007. Each of those applications is hereby incorporated herein by reference in its entirety for all purposes.

Skeletal muscle is one of the body's most specialized tissues. The cells are striated, long, cylindrical, multinucleate, and unbranched. Force generation is performed by arrays of contractile units, termed sarcomeres or skeletal sarcomeres. The sarcomere is an elegantly organized cellular structure that is composed of interdigitating thin and thick filaments (FIG. 1). The thick filaments are composed of myosin, the protein responsible for transducing the chemical energy of ATP hydrolysis into force and directed movement. The thin filaments are composed of a complex of proteins. Actin is a filamentous polymer and is the substrate upon which myosin pulls during force generation. Bound to actin are a set of regulatory proteins, the troponin complex and tropomyosin, which make the actin-myosin interaction dependent on changes in intracellular $Ca^{2+}$ levels. During muscular contraction, $Ca^{2+}$ levels rise and activate the troponin complex, which undergoes a conformational change to allow myosin to bind actin and generate force.

Troponin, a complex of three polypeptides is an accessory protein that is closely associated with actin filaments in vertebrate muscle. The troponin complex, acts in conjunction with the muscle form of tropomyosin to mediate the $Ca.^{2+}$ dependency of myosin ATPase activity and thereby regulate muscle contraction. The troponin polypeptides T, I, and C, are named for their tropomyosin binding, inhibitory, and calcium binding activities, respectively. Troponin T binds to tropomyosin and is believed to be responsible for positioning the troponin complex on the muscle thin filament. Troponin I binds to actin, and the complex formed by troponins I and T, and tropomyosin, inhibits the interaction of actin and myosin. Troponin C is capable of binding up to four calcium molecules. Studies suggest that when the level of calcium in the muscle is raised, troponin C causes troponin I to loose its hold on the actin molecule, causing the tropomyosin molecule shift, thereby exposing the myosin binding sites on actin and stimulating myosin ATPase activity.

Human skeletal muscle is composed of different types of contractile fiber, classified by their myosin type and termed either slow or fast fibers. Table 1 summarizes the different proteins that make up these types of muscle.

| | Muscle Fiber Type | |
|---|---|---|
| | Fast skeletal | Slow Skeletal |
| Myosin Heavy Chain | IIa, (IIb*), IIx/d | Cardiac β |
| Troponin I (TnI) | TnI fast SK | TnI slow SK |
| Troponin T (TnT) | TnT fast SK | TnT slow SK |
| Troponin C (TnC) | TnC fast SK | TnC slow/cardiac |
| Tropomyosin | TM-β/TM-α/TPM 3 | TM-β/TM-αs |

In healthy humans most skeletal muscles are composed of both fast and slow fibers, although the proportions of each vary with muscle types. Slow skeletal fibers, often called type I muscles have more structural similarity with cardiac muscle and tend to be used more for fine and postural control. They usually have a greater oxidative capacity and are more resistant to fatigue with continued use. Fast skeletal muscle fibers are divided into fast oxidative (IIa) and fast glycolytic (type IIx/d) fibers. While these muscle fibers have different myosin types, they share many components including the troponin and tropomyosin regulatory proteins. Fast fibers tend to exert greater forces but fatigue faster than slow fibers and are functionally useful for acute, large scale movements such as rising from a chair or correcting falls.

Muscle contraction and force generation is controlled through nervous stimulation by innervating motor neurons. Each motor neuron may innervate many (approximately 100-380) muscle fibers as a contractile whole, termed a motor unit. When a muscle is required to contract, motor neurons send stimuli as nerve impulses (action potentials) from the brain stem or spinal cord to the each fiber within the motor unit. The contact region between nerve and muscle fibers is a specialized synapse called the neuromuscular junction (NMJ). Here, membrane depolarizing action potentials in the nerve are translated into an impulse in the muscle fiber through release of the neurotransmitter acetylcholine (ACh). ACh triggers a second action potential in the muscle that spreads rapidly along the fiber and into invaginations in the membrane, termed t-tubules. T-tubules are physically connected to $Ca^{2+}$ stores within the sarcoplasmic reticulum (SR) of muscle via the dihydropyridine receptor (DHPR). Stimulation of the DHPR activates a second $Ca^{2+}$ channel in the SR, the ryanodine receptor, to trigger the release of $Ca^{2+}$ from stores in the SR to the muscle cytoplasm where it can interact with the troponin complex to initiate muscle contraction. If muscle stimulation stops, calcium is rapidly taken back up into the SR through the ATP dependent $Ca^{2+}$ pump, SERCA.

Muscle function can become compromised in disease by many mechanisms. Examples include the frailty associated with extreme old age (termed sarcopenia) and muscle wasting that occurs in late stage heart failure and cancer (cachexia). Possibly the most severe form of muscular dysfunction arises from diseases of the motor neurons such as Spinal Muscular Atrophy (SMA) and Amyotrophic Lateral Sclerosis (ALS). Both conditions cause progressive death of motor neurons through causes that are not clear. Surviving motor units attempt to compensate for dying ones by innervating more fibers (termed sprouting) but this can only partially correct muscle function, as muscles are subsequently more prone to problems of coordination and fatigue. Eventually, surviving motor neurons die, resulting in complete paralysis of the affected muscle. Both diseases are commonly fatal through the eventual loss of innervation to the diaphragm, resulting in respiratory failure. SMA is a genetic disorder that arises through the mutation of a protein, SMN1, that appears to be required for the survival and health of motor neurons. The disease is most common in children as the majority of patients only survive until 11-12 years of age. ALS is a disease that arises later in life (Age 50+) and has a rapid progression from initial limb weakness to paralysis and death. Common life expectancy after diagnosis is 3-5 years. The cause of disease for most ALS patients is unknown (termed the spontaneous form) while a small proportion of patients have an inherited form (familial) of disease. Treatment options for both SMA and ALS are limited at this point.

Provided is a method of identifying a candidate agent as a skeletal muscle activator, said method comprising a) adding in vitro the candidate agent to a skeletal sarcomere or target protein complex that directly or indirectly produces ADP or phosphate under conditions which normally allow the production of ADP or phosphate;

b) subjecting the skeletal sarcomere or target protein complex to an enzymatic reaction that uses said ADP or phosphate as a substrate under conditions which normally allow the ADP or phosphate to be utilized;

c) determining the level of activity of the enzymatic reaction of step b, wherein an increase in activity in the presence of the candidate agent compared to the absence of said candidate agent is an indication that the candidate agent activates skeletal muscle.

Also provided is a method of increasing a function or activity of skeletal muscle, said method comprising contacting said skeletal muscle with a candidate agent described herein.

Also provided is a method of increasing efficiency of skeletal muscle, comprising selectively binding troponin C in the troponin complex of fast skeletal muscle fiber whereby the efficiency of skeletal muscle is enhanced.

Also provided is a method for increasing time to fast skeletal muscle fiber fatigue, comprising selectively binding troponin C in troponin complex of fast skeletal muscle fiber; and allowing said fast skeletal muscle fiber to respond with enhanced force and increased time to fatigue as compared to fast skeletal muscle fiber having at least some troponin C which is not selectively bound. In some embodiments, said fast skeletal muscle fiber is allowed to respond with enhanced force and increased time to fatigue, as compared to fast skeletal muscle fiber having at least some troponin C which is not selectively bound to calcium.

Also provided is a method for sensitizing a fast skeletal muscle fiber to produce force in response to lower concentrations of calcium ion, comprising selectively binding troponin C in the sarcomere of said fast skeletal muscle fiber and increasing the sensitivity of said sarcomere to calcium ion, whereby the fast skeletal muscle fiber produces force in response to lower concentrations of calcium ion.

Also provided is a method for increasing time to skeletal muscle fatigue, comprising selectively binding troponin C in the troponin complex of the sarcomere of fast skeletal muscle fiber at a first calcium ion concentration to form a bound complex; and activating said fast skeletal muscle fiber with said bound complex; whereby said fast skeletal muscle fiber responds with enhanced force and/or increased time to fatigue as compared to fast skeletal muscle fiber exposed to said first calcium ion concentration but not comprising said bound complex Other aspects and embodiments will be apparent to those skilled in the art from the following detailed description.

Figure 1:
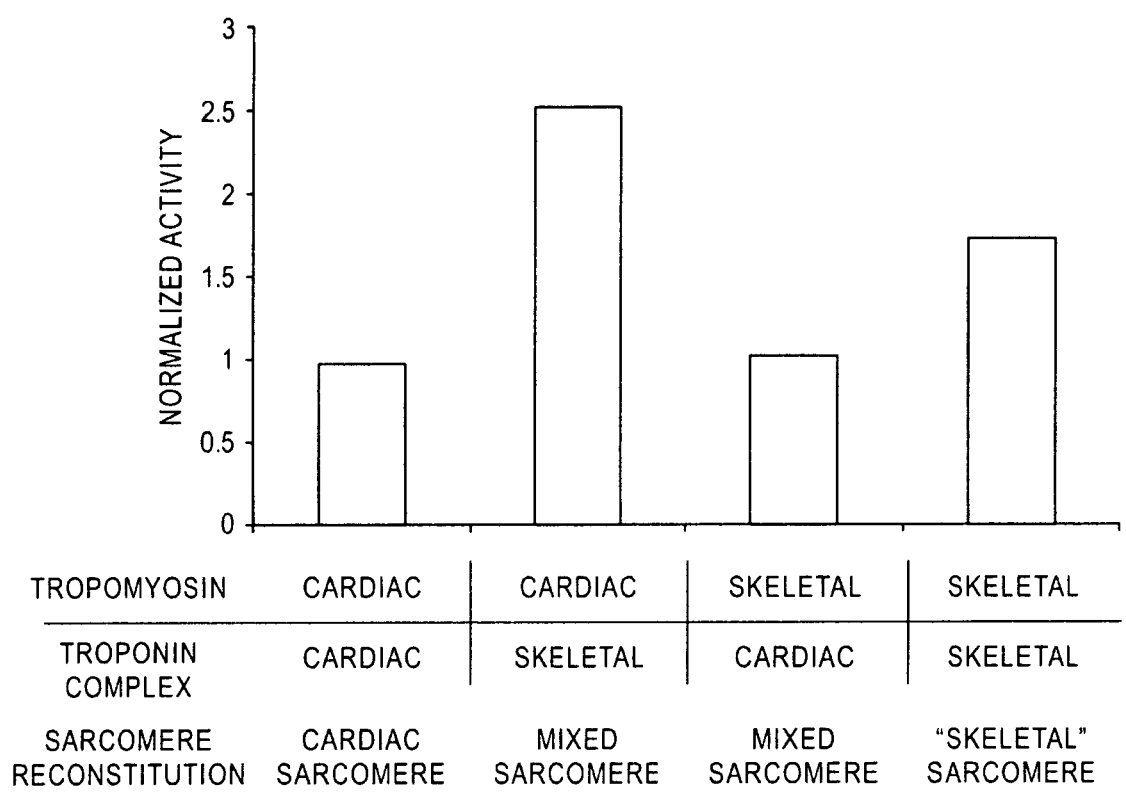
FIG. 1. Target identification of a skeletal muscle activator.

It is to be understood that both the foregoing general description and the following detailed description are exemplary and explanatory only and are not restrictive of the invention, as claimed. In this application, the use of the singular includes the plural unless specifically stated otherwise. In this application, the use of "or" means "and/or" unless specifically stated otherwise. Furthermore, the use of the term "including", as well as other forms, such as "includes" and "included", is not limiting. The use of the term "portion" may include part of a moiety or the entire moiety. Also, terms such as "element" or "component" encompass both elements and components comprising one unit and elements and components that comprise more than one subunit unless specifically stated otherwise.

As used in the present specification, the following words and phrases are generally intended to have the meanings as set forth below, except to the extent that the context in which they are used indicates otherwise.

As used herein, "skeletal muscle activator" refers to a chemical entity that enhances at least one aspect of skeletal muscle function or activity, such as power output, skeletal muscle force, skeletal muscle endurance, oxygen consumption, efficiency, calcium sensitivity, and the like.

Non-limiting examples of skeletal muscle activators are provided in (1) U.S. application Ser. No. 11/888,902, filed Aug. 1, 2007; which claims the benefit of priority to U.S. Provisional Application No. 60/835,272, filed Aug. 2, 2006, and U.S. Provisional Application No. 60/921,054, filed Mar. 30, 2007; (2) U.S. Provisional Application No. 61/026,076, filed Feb. 4, 2008; (3) U.S. Provisional Application No. 61/026,067, filed Feb. 4, 2008; (4) International Application No. PCT/US07/17191, filed Jul. 31, 2007; which claims the benefit of priority to U.S. Provisional Application No. 60/834,906, filed Aug. 1, 2006, U.S. Provisional Application No. 60/836,747, filed Aug. 9, 2006, and U.S. Provisional Application No. 60/920,921, filed Mar. 30, 2007; and (5) U.S. application Ser. No. 12/058,127, filed Mar. 28, 2008, which claims priority to U.S. Provisional Application No. 60/920,994, filed Mar. 30, 2007 and to U.S. Provisional Application No. 61/026,500, filed Feb. 6, 2008. Each of those applications is hereby incorporated herein by reference in its entirety for all purposes.

As used herein, "skeletal muscle" includes skeletal muscle tissue as well as components thereof, such as skeletal muscle fibers (i.e., fast or slow skeletal muscle fibers), the myofibrils comprising the skeletal muscle fibers, the skeletal sarcomere which comprises the myofibrils, and the various components of the skeletal sarcomere described above. Skeletal muscle does not include cardiac muscle or a combination of sarcomeric components that occurs in such combination only in cardiac muscle.

As used herein, "target protein" or "target protein complex" refers to a protein or combination of proteins that directly or indirectly produces ADP or phosphate. In some embodiments the target protein complex is a biochemically functional skeletal sarcomere preparation comprising skeletal myosin, actin, and regulatory proteins. In some embodiments the target proteins include, but are not limited to, skeletal myosin, actin, tropomyosin, and the troponin complex, or components thereof. In some embodiments fragments of these proteins are used. In some embodiments at least one of the target proteins is derived from mammalian cells.

As used herein, the terms "isolated", "purified", or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography, for example.

As used herein, the terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

As used herein, "candidate agent" (used interchangeably herein with "test composition" and "compound" and "test agent") refers to a molecule or composition whose effect on target proteins, a sarcomere, a muscle fiber, or a muscle it is desired to assay. The "candidate agent" can be any molecule or mixture of molecules, optionally in a suitable carrier.

As used herein, "ATPase" refers to an enzyme that hydrolyzes ATP. ATPases include proteins comprising molecular motors such as myosins.

As used herein, "selective binding" or "selectively binding" refers to preferential binding to a target protein in one type of muscle or muscle fiber as opposed to other types. For example, a compound selective binds if that compound preferentially binds troponin C in the troponin complex of a fast skeletal muscle fiber or sarcomere in comparison with troponin C in the troponin complex of a slow muscle fiber or sarcomere or with troponin C in the troponin complex of a cardiac sarcomere.

As used herein, "patient" refers to an animal, such as a mammal, for example a human, that has been or will be the object of treatment, observation or experiment. The methods described herein can be useful in both human therapy and veterinary applications.

As used herein, the term "therapeutic" refers to a compound that is believed to be capable of modulating the contractility of the skeletal sarcomere, skeletal muscle fiber, or skeletal muscle in vivo that can have application in both human or animal disease. Modulation would be desirable in a number of conditions or diseases, including, but not limited to, neuromuscular disorders (e.g., ALS), conditions having muscle wasting (e.g., sarcopenia and cachexia syndromes), claudication, frailty, metabolic syndrome, muscle atrophy associated with disuse, muscle spasms, obesity, and other acute and chronic conditions and diseases.

"Disease" refers to a disease, disorder, condition, symptom, or indication.

The term "effective amount" means an amount that achieves the desired result. The term "therapeutically effective amount" means an amount effective, when administered to a human or non-human patient, to treat a disease, e.g., a therapeutically effective amount may be an amount sufficient to treat a disease responsive to activation of skeletal muscle. The therapeutically effective amount may be ascertained experimentally, for example by assaying blood concentration of the chemical entity, or theoretically, by calculating bioavailability.

As used herein, "frailty" is a syndrome characterized by meeting at least one of the following five attributes: unintentional weight loss, muscle weakness, slow walking speed, exhaustion, and low physical activity.

As used herein, "cachexia" means a state often associated with cancer or other serious diseases or conditions, (e.g, chronic obstructive pulmonary disease, chronic kidney disease), that is characterized by progressive weight loss, muscle atrophy and fatigue, due to the deletion of adipose tissue and skeletal muscle.

As used herein, "muscle spasm" means an involuntary contraction of a muscle. Muscle spasms may lead to cramps.

As used herein, "post-surgical muscle weakness" refers to a reduction in the strength of one or more muscles following surgical procedure. Weakness may be generalized (i.e. total body weakness) or localized to a specific area, side of the body, limb, or muscle.

As used herein, "post-traumatic muscle weakness" refers to a reduction in the strength of one or more muscles following a traumatic episode (e.g. bodily injury). Weakness may be generalized (i.e. total body weakness) or localized to a specific area, side of the body, limb, or muscle.

As used herein, "neuromuscular disease" means any disease or condition that affects any part of the nerve and muscle. Neuromuscular disease encompasses critical illness polyneuropathy, prolonged neuromuscular blockade, acute myopathy as well as acute inflammatory demyelinating polyradiculoneuropathy, amyotrophic lateral sclerosis (ALS), autonomic neuropathy, Charcot-Marie-Tooth disease and other hereditary motor and sensory neuropathies, chronic inflammatory demyelinating polyradiculoneuropathy, dermatomyositis/polymyositis, diabetic neuropathy, dystrophinopathies, endocrine myopathies, focal muscular atrophies, hemifacial spasm, hereditary neuropathies of the Charcot-Marie-Tooth disease type, inclusion body myositis, Kennedy disease, Lambert-Eaton myasthenic syndrome, muscular dystrophy (e.g., limb-girdle, Duchenne, Becker, myotonic, facioscapulohumeral, etc.), metabolic myopathies, metabolic neuropathy, multifocal motor neuropathy with conduction blocks, myasthenia gravis, neuropathy of Friedreich Ataxia, neuropathy of leprosy, nutritional neuropathy, periodic paralyses, primary lateral sclerosis, restrictive lung disease, sarcoidosis and neuropathy, Schwartz-Jampel Syndrome, spinal muscle atrophy, stiff person syndrome, thyroid disease, traumatic peripheral nerve lesions, vasculitic neuropathy, among others.

As used herein "obesity" means having a body mass index (BMI) greater than or equal to 30 kg/m$^2$. BMI is defined as weight (kg) divided by height (m$^2$). Obesity encompasses hyperplastic obesity, an increase in the number of fat cells, and hypertrophic obesity, an increase in the size of the fat cells. Overweight is defined as having a BMI from 25 up to 30 kg/m$^2$; obesity as a BMI greater than or equal to 30 kg/m$^2$, as stated above, and severe (or morbid) obesity is defined as a BMI greater than or quality to 40 kg/m$^2$.

As used herein, "sarcopenia" means a loss of skeletal muscle mass, quality, and strength. Often sarcopenia is associated with ageing, but may also occur in association with HIV infection and a variety of chronic conditions. Sarcopenia may lead to frailty, for example, in the elderly.

As used herein, "wasting syndrome" means a condition characterized by involuntary weight loss associated with chronic fever and diarrhea. In some instances, patients with wasting syndrome lose 10% of baseline body weight within one month.

As used herein, "efficiency" or "muscle efficiency" means the ratio of mechanical work output to the total metabolic cost.

As used herein, "power output" of a muscle means work/cycle time and may be scaled up from PoLo/cycle time units based on the properties of the muscle. Power output may be modulated by changing, for example, activating parameters during cyclical length changes, including timing of activation (phase of activation) and the period of activation (duty cycle.)

Provided is a method of identifying a candidate agent as a skeletal muscle activator, said method comprising a) adding in vitro the candidate agent to a skeletal sarcomere or target protein complex that directly or indirectly produces ADP or phosphate under conditions which normally allow the production of ADP or phosphate;

b) subjecting the skeletal sarcomere or target protein complex to an enzymatic reaction that uses said ADP or phosphate as a substrate under conditions which normally allow the ADP or phosphate to be utilized;

c) determining the level of activity of the enzymatic reaction of step b, wherein an increase in activity in the presence of the candidate agent compared to the absence of said candidate agent is an indication that the candidate agent activates skeletal muscle.

Also provided are systems for identifying skeletal muscle activators. In some embodiments, the systems comprise a target protein complex that is a biochemically functional skeletal sarcomere preparation. The functional biochemical behavior of the sarcomere, including calcium sensitivity of ATPase hydrolysis, may be reconstituted from purified individual components. Since all the regulatory components are present, this system allows for simultaneous screening of the entire protein machinery at once.

In some embodiments, the target protein complex is a biochemically functional sarcomere comprising skeletal myosin, actin, tropomyosin, and the troponin complex. Target proteins include, but are not limited to, skeletal myosin, actin, tropomyosin, and troponin. Suitable target proteins also include fragments of these proteins.

Using standard purification techniques (Margossian S S and Lowey S. (1982) Methods Enzymol 85:55-71), adapted to yield larger quantities of protein, gram quantities of myosin, actin, and the regulatory proteins may be obtained. The myosin may be treated with chymotrypsin to generate the S1 fragment; as opposed to intact myosin, S1 is a soluble protein at salt concentrations necessary for ATPase determination. These proteins can be combined in the proper ratios to reconstitute calcium regulated myosin ATPase activity. In some embodiments an ATPase activation ratio of between about 5 and 20 fold is obtained. In some embodiments a ratio of up to about 10 fold is obtained. This highly regulated sarcomere can be prepared in reliably in large quantities and used for high throughput screening, among other uses.

In some embodiments, the target protein is isolated skeletal myosin. In some embodiments, the methods involve the identification of compounds that activate the myosin ATPase in the absence of actin. In some embodiments, such activators are capable of increasing the basal rate of activity of myosin and thus, could cause the skeletal muscle to increase its rate of metabolism or to burn energy without the need for exercise. Compounds that increase the basal ATPase activity of myosin would find use, for example, in the treatment of obesity, frailty, etc. as discussed further below.

In some embodiments, activity is measured by the methods disclosed in U.S. Pat. No. 6,410,254 which is incorporated herein by reference in its entirety. In some embodiments, those methods are used in multiwell plate formats and are suited for high throughput screening systems to identify lead compounds for medical therapeutic use and can also be used for diagnostics. In some embodiments, ADP or phosphate is used as the readout for protein activity.

The ADP or phosphate level can be monitored using coupling enzyme systems to result in changes in the absorbance or fluorescence of the assay mixture relative to a control mixture to determine if the test compound or mixture of test compounds has an affect on the protein function. This may be done with a single measurement but is preferably done with multiple measurements of the same sample at different times. In the case of multiple measurements, the absolute rate of the protein activity can be determined, and such measurements have higher specificity particularly in the presence of test compounds that have similar absorbance or fluorescence properties to that of the enzymatic readout.

In some embodiments, the target protein complex comprises a biochemically functional skeletal sarcomere. Compounds which modulate the activity of the complex or one or more of the proteins thereof can be found by monitoring the production of either ADP or phosphate by a variety of methods.

There are several mechanisms by which candidate agents might modulate the target protein complex. One might increase the rate at which myosin hydrolyzes ATP. Since, ATP hydrolysis is coupled to force production, this increase would be expected to increase the force of muscle contraction. In the presence of actin, myosin ATPase activity is stimulated >100 fold. Thus, ATP hydrolysis not only measures myosin enzymatic activity but also its interaction with the actin filament. Thus, a compound that modulates the function of the target protein complex is identified by an increase or decrease in the rate of ATP hydrolysis compared to a control assay in the absence of that compound.

One method for monitoring ADP production is to couple the ADP production to NADH oxidation with the enzymes pyruvate kinase and lactate dehydrogenase and to monitor the NADH level either by absorbance or fluorescence (Nature 1956 178:632; Mol Pharmacol 1970 January; 6(1):31-40). One method for monitoring phosphate production is to use purine nucleoside phosphorylase to couple the phosphate production to the cleavage of a purine analog which results in either a change in absorbance (Proc Natl Acad Sci USA 1992 Jun. 1; 89(11):4884-7) or fluorescence (Biochem J 1990 266 (2):611-4). With either method, the rate of ATP hydrolysis by the target protein complex of interest can be measured.

In some embodiments, for example for use with myosin as the target protein, the level of activity of the enzymatic reaction can be accomplished using an absorbance assay, such as the one described above with a longer read time, or a luminescence assay, such as those known in the art.

Test compounds can be assayed in a highly parallel fashion by using multiwell plates by placing the compounds either individually in wells or testing them in mixtures. Assay components including the target protein complex, coupling enzymes and substrates, and ATP can then be added to the wells and the absorbance or fluorescence of each well of the plate can be measured with a plate reader.

In some embodiments, the method uses a 384 well plate format and a 25 .mu.L reaction volume. A pyruvate kinase/lactate dehydrogenase coupled enzyme system (Huang T G and Hackney D D. (1994) J Biol Chem 269(23):16493-501, which is incorporated herein by reference) is used to measure the rate of ATP hydrolysis in each well. As will be appreciated by those in the art, the assay components are added in buffers and reagents. Since the methods outlined herein allow kinetic measurements, the incubation periods may be optimized to give adequate detection signals over the background. The assay may be done in real time giving the kinetics of ATP hydrolysis which increases the signal to noise ratio of the assay.

Candidate agents encompass numerous chemical classes, though typically they are organic molecules, preferably small organic molecules having a molecular weight of more than 100 and less than about 2,500 daltons. Candidate agents are obtained from a wide variety of sources including libraries of synthetic or natural compounds. They include peptides, macromolecules, small molecules, chemical and/or biological mixtures, and fungal, bacterial, or algal extracts. Such compounds, or molecules, may be either biological, synthetic organic, or even inorganic compounds, and may be obtained from several sources, including pharmaceutical companies and specialty suppliers of libraries (e.g., combinatorial libraries) of compounds.

Methods described herein are well suited, for example, for screening libraries of compounds in multiwell plates (e.g., 96-well plates), with a different test compound in each well. In particular, the methods may be employed with combinatorial libraries. A variety of combinatorial libraries of random-sequence oligonucleotides, polypeptides, or synthetic oligomers have been proposed. A number of small-molecule libraries have also been developed.

Combinatorial libraries may be formed, for example, by a variety of solution-phase or solid-phase methods in which mixtures of different subunits are added stepwise to growing oligomers or parent compounds, until a desired compound is synthesized. A library of increasing complexity can be formed in this manner, for example, by pooling multiple choices of reagents with each additional subunit step.

The identity of library compounds with desired effects on the target protein complex can be determined by conventional means, such as iterative synthesis methods in which sublibraries containing known residues in one subunit position only are identified as containing active compounds.

Methods to identify the chemical entities as binding to a protein or as a modulator of the binding characteristics or biological activity of a protein are described in, for example, U.S. Pat. No. 6,410,254 and U.S. patent application Ser. No. 10/987,165.

For example, test compounds can be assayed in a highly parallel fashion by using multiwell plates by placing the compounds either individually in wells or testing them in mixtures. Assay components including the target protein complex, coupling enzymes and substrates, and ATP can then be added to the wells and the absorbance or fluorescence of each well of the plate can be measured with a plate reader.

In some embodiments, the method uses a 384 well plate format and a 25 µL reaction volume. A pyruvate kinase/lactate dehydrogenase coupled enzyme system (Huang T G and Hackney D D. (1994) J Biol Chem 269(23):16493-501) can be used to measure the rate of ATP hydrolysis in each well. As will be appreciated by those in the art, the assay components are added in buffers and reagents. The incubation periods can be optimized to give adequate detection signals over the background. The assay can be done in real time giving the kinetics of ATP hydrolysis which increases the signal to noise ratio of the assay.

The compounds can be further tested using skinned muscle fiber preparations. Such assays are known in the art. See, e.g., Cheung et al. (2002) Nature Cell Biol. 4:83 and U.S. Patent Publication No. 20020006962.

Also provided are methods for enhancing skeletal muscle efficiency in a patient in need thereof, comprising administering to said patient an effective amount of a compound that selectively binds the troponin complex of fast skeletal muscle fiber or sarcomere. In some embodiments, the compound selectively binds troponin C in the troponin complex of fast skeletal muscle fiber or sarcomere. In some embodiments, the compound activates fast skeletal muscle fiber or sarcomere. In some embodiments, administration of the compound results in an increase in skeletal muscle power output. In some embodiments, administration of the compound results in increased sensitivity of the fast skeletal muscle fiber or sarcomere to calcium ion, as compared to skeletal muscle fiber or sarcomere untreated with the compound. In some embodiments, administration of the compound results in a lower concentration of calcium ions results in the binding of skeletal muscle myosin to actin. In some embodiments, administration of the compound results in the fast skeletal muscle fiber generating force more efficiently at submaximal levels of muscle contraction.

Also provided is a method for sensitizing a fast skeletal muscle fiber to produce force in response to lower concentrations of calcium ion, comprising contacting the fast skeletal muscle fiber with a compound that selectively binds to troponin C in fast skeletal muscle sarcomere. In some embodiments, contacting the fast skeletal muscle fiber with the compound results in activation of the fast skeletal muscle fiber at a lower calcium ion concentration than in an untreated fast skeletal muscle fiber. In some embodiments, contacting the fast skeletal muscle fiber with the compound results in the production of increased force at a lower calcium ion concentration in comparison with an untreated fast skeletal muscle fiber.

Also provided is a method for increasing time to skeletal muscle fatigue in a patient in need thereof, comprising contacting fast skeletal muscle fiber with a compound that selectively binds to troponin C in the troponin complex of the fast skeletal muscle fiber. In some embodiments, the compound binds to form a ligand-troponin complex-calcium ion complex that activates the fast skeletal muscle fiber. In some embodiments, formation of the complex and/or activation of the fast skeletal muscle fiber results in enhanced force and/or increased time to fatigue as compared to untreated fast skeletal muscle contacted with a similar calcium ion concentration.

The skeletal muscle activators are administered at a therapeutically effective dosage, e.g., a dosage sufficient to provide treatment for the disease states previously described. While human dosage levels have yet to be optimized for the chemical entities described herein, generally, a daily dose ranges from about 0.05 to 100 mg/kg of body weight; in certain embodiments, from about 0.10 to 10.0 mg/kg of body weight, and in certain embodiments, from about 0.15 to 1.0 mg/kg of body weight. Thus, for administration to a 70 kg person, in certain embodiments, the dosage range would be about from 3.5 to 7000 mg per day; in certain embodiments, about from 7.0 to 700.0 mg per day, and in certain embodiments, about from 10.0 to 100.0 mg per day. The amount of the chemical entity administered will, of course, be dependent on the subject and disease state being treated, the severity of the affliction, the manner and schedule of administration and the judgment of the prescribing physician; for example, a likely dose range for oral administration would be from about 70 to 700 mg per day, whereas for intravenous administration a likely dose range would be from about 70 to 700 mg per day depending on compound pharmacokinetics.

Administration of the skeletal muscle activators described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. In some embodiments, oral or parenteral administration is used.

Pharmaceutically acceptable compositions include solid, semi-solid, liquid and aerosol dosage forms, such as, e.g., tablets, capsules, powders, liquids, suspensions, suppositories, aerosols or the like. The skeletal muscle activators can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The skeletal muscle activators described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see *Remington's Pharmaceutical Sciences*, Mack Publishing Company, Easton, Pa.

In addition, the skeletal muscle activators can be co-administered with, and the pharmaceutical compositions can include, other medicinal agents, pharmaceutical agents, adjuvants, and the like. Suitable medicinal and pharmaceutical agents include modulators of one or more of skeletal myosin, skeletal actin, skeletal tropomyosin, skeletal troponin C, skeletal troponin I, skeletal troponin T, and skeletal muscle, including fragments and isoforms thereof, and the skeletal sarcomere and other suitable therapeutic agents useful in the treatment of the aforementioned diseases including: anti-obesity agents, anti-sarcopenia agents, anti-wasting syndrome agents, anti-frailty agents, anti-cachexia agents, anti-muscle spasm agents, agents against post-surgical and post-traumatic muscle weakness, and anti-neuromuscular disease agents, as well as the agents described in U.S. Patent Application No. 2005/0197367.

Suitable additional medicinal and pharmaceutical agents include, for example: orlistat, sibramine, diethylpropion, phentermine, benzaphetamine, phendimetrazine, estrogen, estradiol, levonorgestrel, norethindrone acetate, estradiol valerate, ethinyl estradiol, norgestimate, conjugated estrogens, esterified estrogens, medroxyprogesterone acetate, insulin-derived growth factor, human growth hormone, riluzole, cannabidiol, prednisone, beta agonists (e.g., albuterol), myostatin inhibitors, selective androgen receptor modulators, nonsteroidal anti-inflammatory drugs, and botulinum toxin.

Other suitable medicinal and pharmaceutical agents include TRH, diethylstilbesterol, theophylline, enkephalins, E series prostaglandins, compounds disclosed in U.S. Pat. No. 3,239,345 (e.g., zeranol), compounds disclosed in U.S. Pat. No. 4,036,979 (e.g., sulbenox), peptides disclosed in U.S. Pat. No. 4,411,890 growth hormone secretagogues such as GHRP-6, GHRP-1 (disclosed in U.S. Pat. No. 4,411,890 and publications WO 89/07110 and WO 89/07111), GHRP-2 (disclosed in WO 93/04081), NN703 (Novo Nordisk), LY444711 Lilly), MK-677 (Merck), CP424391 (Pfizer) and B-HT920, growth hormone releasing factor and its analogs, growth hormone and its analogs and somatomedins including IGF-1 and IGF-2, leukemia inhibitory factor, cilia neurotrophic factor, brain derived neurotrophic factor, interleukin 6, interleukin 15, alpha-adrenergic agonists, such as clonidine or serotonin 5-HT$_D$ agonists, such as sumatriptan, agents which inhibit somatostatin or its release, such as physostigmine, pyridostigmine, parathyroid hormone, PTH(1-34), and bisphosphonates, such as MK-217 (alendronate).

Still other suitable medicinal and pharmaceutical agents include estrogen, testosterone, selective estrogen receptor modulators, such as tamoxifen or raloxifene, other androgen receptor modulators, such as those disclosed in Edwards, J. P. et. al., Bio. Med. Chem. Let., 9, 1003-1008 (1999) and Hamann, L. G. et. al., J. Med. Chem., 42, 210-212 (1999), and progesterone receptor agonists ("PRA"), such as levonorgestrel, medroxyprogesterone acetate (MPA).

Still other suitable medicinal and pharmaceutical agents include aP2 inhibitors, such as those disclosed in U.S. Ser. No. 09/519,079 filed Mar. 6, 2000, PPAR gamma antagonists, PPAR delta agonists, beta 2 adrenergic agonists, beta 3 adrenergic agonists, such as AJ9677 (Takeda/Dainippon), L750355 (Merck), or CP331648 (Pfizer), other beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993, WO 99/00353, and GB98/284425, and anorectic agents, such as dexamphetamine, phentermine, phenylpropanolamine or mazindol.

Still other suitable medicinal and pharmaceutical agents include HIV and AIDS therapies, such as indinavir sulfate, saquinavir, saquinavir mesylate, ritonavir, lamivudine, zidovudine, lamivudine/zidovudine combinations, zalcitabine, didanosine, stavudine, and megestrol acetate.

Still other suitable medicinal and pharmaceutical agents include antiresorptive agents, hormone replacement therapies, vitamin D analogues, elemental calcium and calcium supplements, cathepsin K inhibitors, MMP inhibitors, vitronectin receptor antagonists, Src SH.sub.2 antagonists, vacular —H$^+$-ATPase inhibitors, ipriflavone, fluoride, Tibo lone, pro stanoids, 17-beta hydroxysteroid dehydrogenase inhibitors and Src kinase inhibitors.

The above other therapeutic agents, when employed in combination with the chemical entities described herein, may be used, for example, in those amounts indicated in the Physicians' Desk Reference (PDR) or as otherwise determined by one of ordinary skill in the art.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the skeletal muscle activators may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

The compounds described herein are capable of modulating the contractility of the skeletal sarcomere in vivo and can have application in both human and animal disease. Such compounds may, for example, be capable of increasing basal ATPase rate of skeletal myosin or may increase the power output of skeletal myosin. Modulation would be desirable in a number of conditions or diseases, including, but not limited to, neuromuscular disorders (e.g., ALS), conditions having muscle wasting (e.g., sarcopenia and cachexia syndromes), claudication, frailty, metabolic syndrome, muscle atrophy associated with disuse, muscle spasms, obesity, and other acute and chronic conditions and diseases.

More specifically, the methods can be utilized to identify compounds that inhibit the skeletal sarcomere and thus, useful for the treatment of Amyotrophic Lateral Sclerosis (ALS), myasthenia gravis, spinal muscular atrophy, and multiple sclerosis (MS); for other skeletal muscle convulsion or spasm (such as Parkinson's disease, muscle spasm caused by various pathogenesis, including tetanus, some infectious diseases, some neurological diseases, and toxic spasm, such as poisoning of organophosphorus, and so on); and spasm of muscle tissues of other organs such as opthalmospasm, facial muscle spasm, and so on.

In addition, the treatment of muscular myopathies, such as muscular dystrophies are encompassed by the invention. Muscular dystrophy can be characterized by progressive muscle weakness, destruction and regeneration of the muscle fibers, and eventual replacement of the muscle fibers by fibrous and fatty connective tissue. There is no accumulation of metabolic storage material in the muscle fibers of patients suffering from muscular dystrophy. Treatment according to the invention may alleviate some of the symptoms of the disease and provide improved quality of life for the patients.

The compounds also can be used for the treatment of frailty or sarcopenia, such as that associated with aging. More specifically, clinically, a decline in such skeletal muscle tissue mass, or muscle atrophy, is an important contributor to frailty in older individuals. In human males, muscle mass declines by one-third between the ages of 50 and 80. In older adults, extended hospitalization can result in further disuse atrophy leading to a potential loss of the ability for independent living and to a cascade of physical decline. Moreover, the physical aging process profoundly affects body composition, including significant reductions in lean body mass and increases in central adiposity. In addition, it is possible that the age-associated decrement in muscle mass, and subsequently in strength and endurance, may be a critical determinant for functional loss, dependence and disability. Muscle weakness is also a major factor predisposing the elderly to falls and the resulting morbidity and mortality.

The compounds also may find use in the treatment of disuse atrophy, wasting or cachexia (e.g., in cancer patients), and treatment of chronic diseases or conditions associated with reductions in muscle mass, such as muscle wasting associated with, including but not limited to: hypertension, COPD, heart failure, chronic kidney disease, obesity, claudication, metabolic syndrome, chronic fatigue syndrome, diabetes, and artherosclerotic cardiovascular disease.

The compounds may also find use in the context of patients undergoing rehabilitation, including both in the hospital (e.g., following surgery) and patients undergoing longer term rehabilitation in an outpatient setting.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

EXAMPLES

The following examples serve to more fully describe the manner of using the above-described invention. It is understood that these examples in no way serve to limit the true scope of this invention, but rather are presented for illustrative purposes.

Example 1

Preparation of Sarcomeric Proteins from Skeletal Muscle

Actin was purified by first preparing an ether powder of cardiac muscle (Zot H G and Potter J D. (1981) Preparative Biochemistry 11:381-395) as described below. Subsequently, actin was cycled between the filamentous and soluble state through rounds of centrifugation and dialysis (Spudich J A and Watt S. (1971) J. Biol. Chem. 246:4866-4871). It was stored in the filamentous state at 4° C.

Tropomyosin was extracted from the ether powder and separated from the other proteins based on pH dependent precipitations followed by successive ammonium sulfate cuts at 53% and 65% (Smillie L B. (1981) Methods Enzymol 85 Pt B:234-41). The troponins were isolated as an intact complex of TnC, TnT, and TnI. Ether powder is extracted in a high salt buffer. Successive ammonium sulfate cuts of 30% and 45% were done; the precipitate was solubilized by dialysis into a low salt buffer and then further purified on a DEAE Toyopearl column with a 25-350 mM KCl gradient. There was no measurable ATPase in any of the components except for myosin which naturally had a very low basal ATPase in the absence of actin.

Just prior to screening, the actin, tropomyosin, and troponin complex are mixed together in the desired ratio (e.g., 7:1:1) to achieve maximal calcium regulation of the actin filament. The screen is conducted at a pCa=6.5. This calcium concentration is in the physiological range during muscle contraction.

To measure the generation of ADP during the reaction, a pyruvate kinase/lactate dehydrogenase/NADH coupled enzyme system (PK/LDH) is added to the actin. The myosin is kept separately. The plates are read in real time so that kinetic curves are obtained. These compounds are in DMSO and were already spotted onto the bottoms of 384 well plates at 10 to 40 μg/ml final concentration.

Example 2

Actin Preparation

1. Extract powder (as prepared herein) with 20 ml buffer A (see below, add BME and ATP just prior to use in each of the following steps) per gram of powder (200 ml per 10 g). Use a large 4 L beaker for 150 g of powder. Mix vigorously to dissolve powder. Stir at 4° C. for 30 min.

2. Separate extract from the hydrated powder by squeezing through several layers of cheesecloth. Cheesecloth should be pre-sterilized by microwaving damp for 1-2 min.

3. Re-extract the residue with the same volume of buffer A and combine extracts.

4. Spin in JLA10 rotor(s) for 1 hr at 10K rpm (4° C.). Collect supernatant through 2 layers of cheesecloth.

5. Add ATP to 0.2 mM and $MgCl_2$ to 50 mM. Stir on stir plate at 4° C. for 60 minutes to allow actin to polymerize/form para-crystals.

6. Slowly add solid KCl to 0.6 M (45 g/l). Stir at 4° C. for 30 min.

7. Spin in JLA10 rotor(s) at 10K rpm for 1 hr.

8. Depolymerization: Quickly rinse surface of pellets with buffer A and dispose of wash. Soften the pellets by pre-incubation on ice with small amount of buffer A in each tube (use less than half of final resuspension volume total in all tubes). Resuspend by hand first with cell scraper and combine pellets. Wash tubes with extra buffer using a 25 ml pipette and motorized pipettor, aggressively removing actin from sides of tubes. Homogenize in large dounce in cold buffer A on ice. Use 3 ml per gram of powder originally extracted.

9. Dialyze against buffer A with 4 changes over 48 hour period.

10. Collect dialyzed actin and spin in the 45 Ti rotor at 40K rpm for 1.5 hr (4° C.).

11. Collect supernatant (G-Actin). Save a sample for gel analysis and determination of protein concentration.

To polymerize G-actin for storage add KCl to 50 mM (from 3 M stock), $MgCl_2$ to 1 mM, and $NaN_3$ to 0.02% (from 10% stock). Store at 4° C. Do not freeze.

Buffer A: 2 mM tris/HCl, 0.2 mM $CaCl_2$, 0.5 mM (36 μl/L) 2-mercaptoethanol, 0.2 mM $Na_2$ ATP (added fresh), and 0.005% Na-azide; pH 8.0.

Example 3

Powder Preparation

1. Volumes are given per about 1000 g of the minced muscle.

2. Pre-cut and boil cheesecloth for 10 min in water. Drain and dry.

3. Mince chicken breast in a prechilled meat grinder.

4. Extract with stirring in 2 L of 0.1 M KCl, 0.15 M K-phosphate, pH 6.5 for 10 min at 4° C. Spin 5000 rpm, 10 min, 4° C. in JLA. Collect the pellet.

5. Extract pellets with stirring with 2 L of 0.05 M $NaHCO_3$ for 5 min. Spin 5000 rpm, 10 min, 4° C. in JLA. Collect the pellet. Repeat the extraction once more.

6. Extract the filtered residue with 2 L of 1 mM EDTA, pH 7.0 for 10 min with stirring.

7. Extract with 2 L of $H_2O$ for 5 min with stirring. Spin 10000 rpm, 15 min, 4° C. in JLA. Carefully collect the pellet, part of which will be loose and gelatinous.

8. Extract 5 times with acetone (2 L of acetone for 10 min each with stirring). Squeeze through cheesecloth gently. All acetone extractions are performed at room temperature. Acetone should be prechilled to 4° C.

9. Drying: Place the filtered residue spread on a cheesecloth in a large glass tray and leave in a hood overnight. When the residue is dry, put in a wide mouth plastic bottle and store at 20° C.

Example 4

Alternate Powder Preparation

Based on Zot & Potter (1981) Prep. Biochem. 11(4) pp. 381-395.

1. Dissect left ventricles of the cardiac muscle. Remove as much of the pericardial tissue and fat as possible. Grind in a prechilled meat grinder. Weigh.

2. Prepare 5 volumes of Extract buffer (see below). Be sure the pH=8.0. Then, homogenize the meat in a blender, 4 times 15 sec on blend with 15 secs in between. Do this with 1 volume weight/volume) of buffer taken from the 5 volumes already prepared. Add the homogenate back to the extract buffer and stir until well mixed (5 minutes).

3. Filter through one layer of cheesecloth in large polypropylene strainer. Resuspend back into 5 volumes of extract buffer as above.

4. Repeat Step 3 four more times. At the end, do not resuspend in extraction buffer but proceed to Step 5. The pellets should be yellow white.

5. Resuspend in 3 volumes (according to original weight) of 95% cold ethanol. Stir for 5 min and squeeze through cheesecloth as above, repeat two more times.

6. Weigh squeezed residue and then resuspend in 3 volumes (new weight/volume) of cold diethyl ether.

7. Repeat Step 6 a total of three times.

8. Leave overnight in a single layer on a cheesecloth in a glass tray.

9. When dry, collect the powder, weigh and store in a wide-mouth jar at 4° C.

EXTRACT BUFFER: 50 mM KCl, 5 mM Tris pH 8.0
Prepare as 50 times concentrate:
For 2 L:
250 mM Tris pH 8.0. Tris Base (121.14 g/mol, 60.6 g) pH to 8.0 with conc. HCl, then add:
2.5 M KCl (74.55 g/mol, 372 g)

Example 5

Purification of Skeletal Muscle Myosin

See, Margossian, S. S, and Lowey, S. (1982) Methods Enzymol. 85, 55-123 and Goldmann, W. H. and Geeves, M. A. (1991) Anal. Biochem. 192, 55-58.

Solution A: 0.3 M KCl, 0.15 M potassium phosphate, 0.02 M EDTA, 0.005 M $MgCl_2$, 0.001 M ATP, pH 6.5.

Solution B: 1 M KCl, 0.025 M EDTA, 0.06 M potassium phosphate, pH 6.5.

Solution C: 0.6 M KCl, 0.025 M potassium phosphate, pH 6.5.

Solution D: 0.6 M KCl, 0.05 M potassium phosphate, pH 6.5.

Solution E: 0.15 M potassium phosphate, 0.01 M EDTA, pH 7.5.

Solution F: 0.04 M KCl, 0.01 M potassium phosphate, 0.001 M DTT, pH 6.5.

Solution G: 3 M KCl, 0.01 M potassium phosphate, pH 6.5. All procedures are carried out at 4° C.

Obtain ~1000 g skeletal muscle, such as rabbit skeletal muscle.

1. Grind twice; extract with 2 L solution A for 15 min while stirring; add 4 L cold H2O, filter through gauze; dilute with cold H2O to ionic strength of 0.04, (about 10-fold); let settle for 3 h; collect precipitate at 7,000 rpm in GSA rotor for 15 min.

2. Disperse pellet in 220 ml solution B; dialyze overnight against 6 L solution C; slowly add ~400 ml equal volume cold distilled H2O; stir for 30 min; centrifuge at 10,000 rpm for 10 min in GSA rotor.

3. Centrifuge supernatant at 19,000 rpm for 1 h.

4. Dilute supernatant to ionic strength of 0.04 (~8-fold); let myosin settle overnight; collect about 5-6 L fluffy myosin precipitate by centrifuging at 10,000 rpm for 10 min in GSA rotor.

5. Resuspend pellet in minimal volume of solution G; dialyze overnight against 2 L solution D; centrifuge at 19,000 rpm for 2 h, in cellulose nitrate tubes; puncture tubes and separate myosin from fat and insoluble pellet.

6. Dilute supernatant to 5-10 mg/ml and dialyze against solution E extensively, load onto DEAE-sephadex column.

7. Preequilibrate with solution E; apply 500-600 g myosin at 30 ml/h; wash with 350 ml solution E; elute with linear gradient of 0-0.5 M KCl in solution E (2×1 liter); collect 10 ml fractions; pool myosin fractions (>0.1 M KCl); concentrate by overnight dialysis against solution F; centrifuge at 25,000 rpm for 30 min; store as above.

8. The myosin is then cut with chymotrypsin or papain in the presence of EDTA to generate the S1 fragment which is soluble at the low salt conditions optimal for ATPase activity (Margossian supra).

Example 6

Activation of Fast Skeletal Muscle Fibers

Fast fiber activators were identified by measuring the enzymatic activity of muscle myofibril preparations using the proprietary PUMA™ (see, e.g., U.S. Pat. Nos. 6,410,254, 6,743,599, 7,202,051, and 7,378,254) assay system. Myofibril preparations consisted of rabbit skeletal muscle (approximately 90% fast fibers) that had been treated with a detergen (triton X-100) to remove cellular membranes and then homogenized. This preparation retained all of the sarcomeric components in a native conformation and the enzymatic activity was still regulated by calcium. That preparation was screened with a library of 244,000 small molecules using a myofibril suspension and a level of calcium sufficient to increase enzymatic activity of the myofibrils to 25% of their maximal rate (termed pCa25%). Enzymatic activity was tracked via a kinetic assay with a UV absorption readout. Hits were identified as compounds that increased the rate of enzymatic activity by greater than 40% at 40 µM. Myofibril preparations are calcium regulated and were screened at a level of calcium sufficient to produce a 25% increase in enzymatic rate. Detergent treated myofibrils in 384 well-plates were incubated with 500 µM ATP and 40 µM compound and a kinetic read of UV absorbance performed. Data was normalized to control wells.

Example 7

Activation of Skeletal Muscle Fibers

The ability of a compound to increase the observed enzymatic rate in an in vitro sarcomere assay could arise either from increased enzymatic activity at the level of the myosin motor or from increased sensitivity of a decorated actin filament to calcium activation. To distinguish between these two possible modes of action, a "mix and match" sarcomere component swap experiment was performed. This assay used purified individual components of cardiac and skeletal sarcomeres (an active fragment of myosin, tropomyosin, the troponin complex and actin) and reconstituted calcium regulated myofibrils of mixed composition. Using this technique with compounds that were not active against cardiac myofibrils it was possible to discriminate between activity of the compound on the myosin motor (the thick filament) or on the regulatory apparatus (the thin filament). Experiments with a skeletal muscle activator revealed that the target of this compound was the troponin regulatory complex (FIG. 1). In those experiments the maximal enzymatic rate of sarcomere preparations was measured after reconstitution of purified components from different tissue types. All sarcomere preparations consisted of 0.5 µM recombinant motor domain (S1) of bovine myosin and 14 µM purified bovine cardiac actin. Tropomyosin and troponin complexes were purified from either bovine cardiac or rabbit skeletal muscle in a 1:1 ratio. Reconstituted preparations were incubated with vehicle (DMSO) or 20 µM skeletal muscle activator at pCa25% and maximal enzymatic rate recorded. Data shown is normalized to rates obtained from vehicle controls. Additional studies with other skeletal muscle activators also show activity tracking with the skeletal troponin complex.

Example 8

Activation of Skeletal Muscle Fibers

Figure 2A:
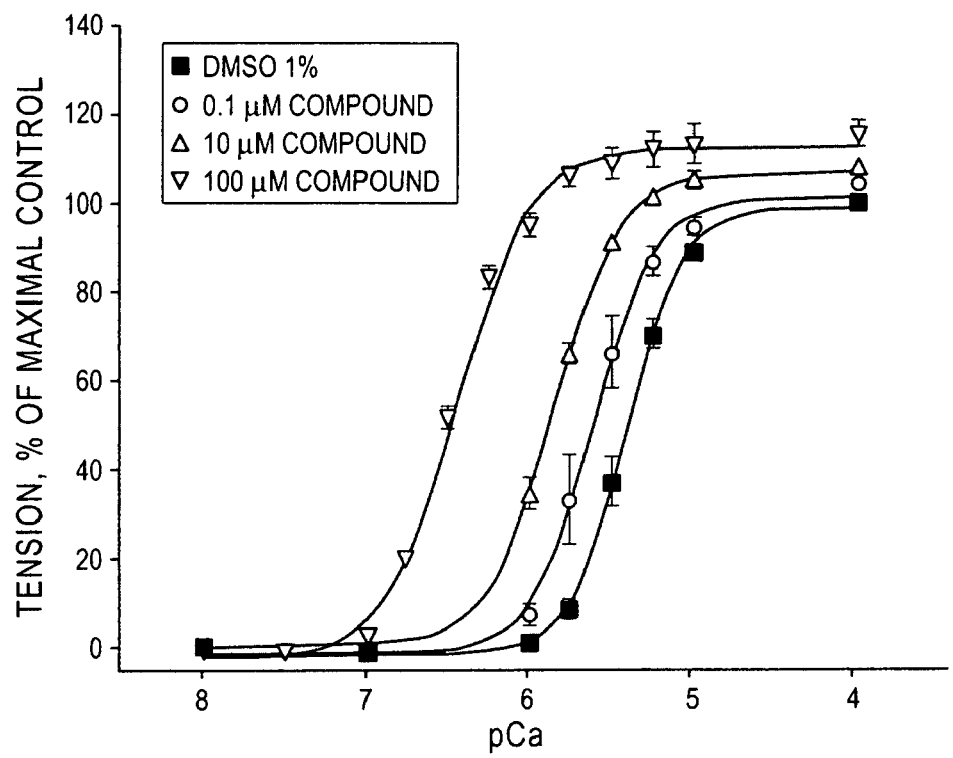
FIG. 2A. Effect of a skeletal muscle activator on skinned skeletal fibers from Rabbit psoas muscle.
Figure 2B:
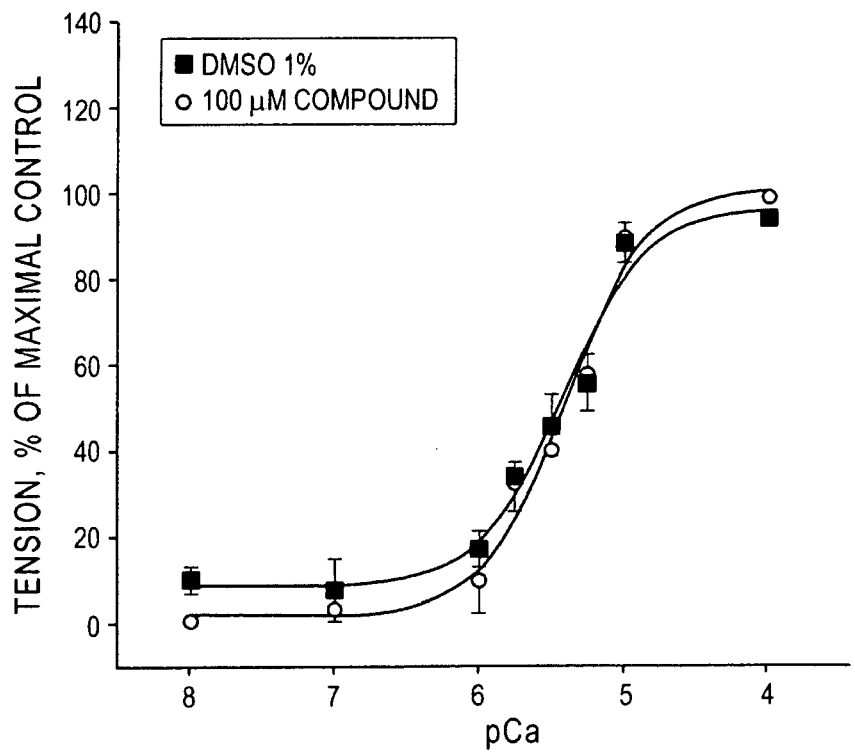
FIG. 2B. Effect of a skeletal muscle activator on skinned skeletal fibers from Rabbit semimembranosus muscle
FIGS. 3A and 3B. Effect of a skeletal muscle activator on isometric force in rat FDB fibers.

This example demonstrates that ability of the compounds to increase the contractile force in a fast skeletal muscle fiber. These properties were investigated by measuring contractile force in detergent permeabilized skeletal muscle fibers, also known as skinned skeletal fibers. These skeletal fibers retain their intrinsic sarcomeric organization but all aspects of cellular calcium cycling no longer exist. If single skinned fibers are attached to a sensitive force transducer, developed force can be measured after fibers are treated with buffered solutions containing calcium (FIG. 2). To generate the data shown in FIG. 2, muscle was excised and skinned in a solution containing 0.5% brij-58 at 4° C. for 30 minutes. It was then transferred to a storage solution for 48 hrs at −20° C. Single fibers were attached to a model 400A force transducer (Aurora Scientific) at 10° C. in a 20 µM MOPS, 132 µM potassium acetate relaxing buffer and force measured after incubation with increasing concentration of buffered calcium and the indicated concentration a skeletal muscle activator (added as a DMSO stock, final concentration DMSO 1%). Force is plotted as a percent of maximal contraction measured at pCa 4 (n=3, each curve).

These preparations have two advantages over live muscle. First, the cellular membrane is not a barrier to compound penetration. Second, any increase in contractile force must be related to a direct effect on the sarcomeric proteins rather than an alteration in intracellular calcium levels since calcium concentration is controlled.

Treatment of fast skinned fibers from rabbit psoas muscle with a skeletal muscle activator revealed a dose-dependent increase in fiber sensitivity to calcium without significantly increasing maximal force generation or the shape of the force/calcium curve (or 'pCa' curve). This is consistent with a compound that targets the troponin complex as it should increase sensitivity to calcium without altering the enzymatic activity of myosin. Specificity of these compounds for fast skeletal fibers was confirmed by repeating skinned fiber measurements with slow skeletal fibers isolated from the rabbit semimembranosus muscle.

Example 9

Activation of Fast Skeletal Muscle Fibers

Figure 3A:
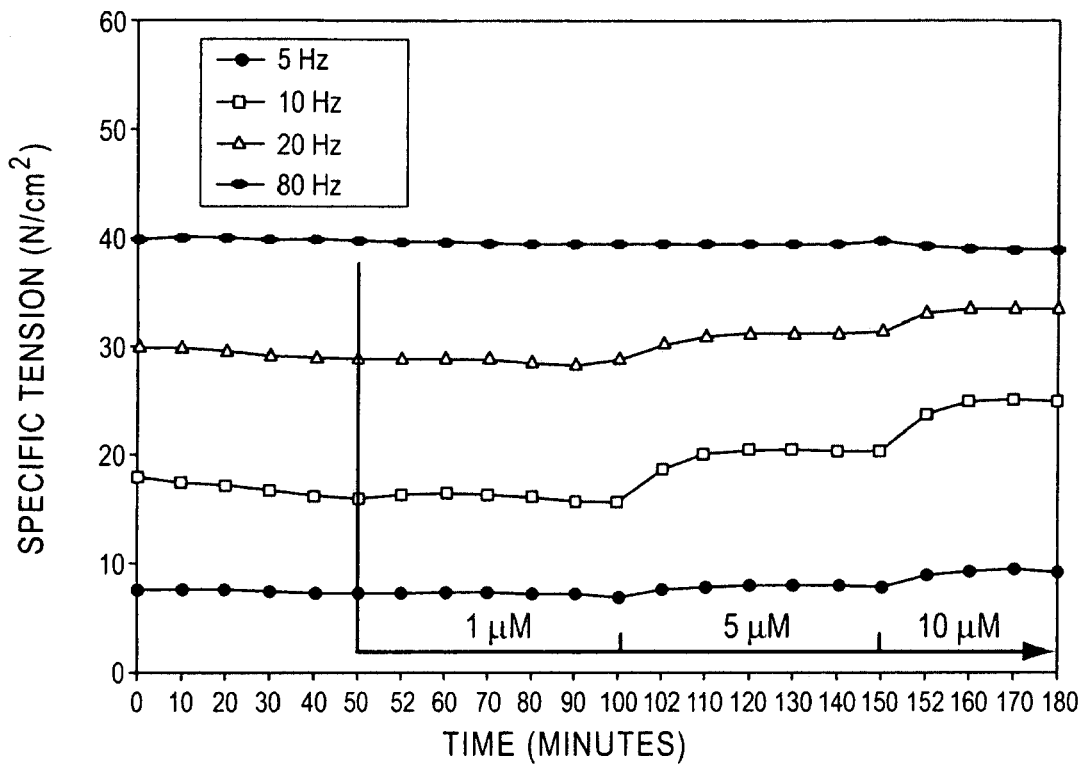
Figure 3B:
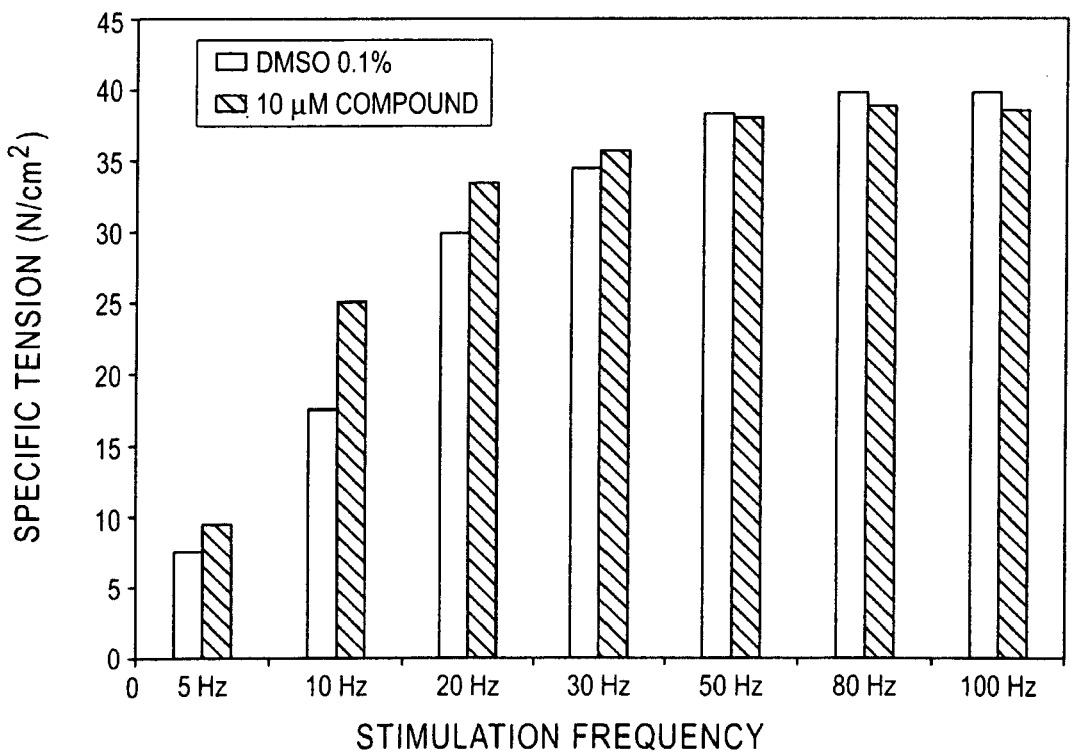

This Example confirms live skeletal muscle activity of the compounds in-vitro. The flexor digitorum brevis (FDB) muscle was used for these studies. The FDB is a predominantly (85%) fast fiber muscle from the hind feet of the rat. It was found that this muscle has a discreet branch leading to the small digit which could be dissected free from the main muscle with its own tendons intact. Upon dissection, tissue was bathed in oxygenated Krebs bicarbonate solution with 0.1% DMSO vehicle at 20° C. and attached to a force transducer (Aurora Scientific, Ontario, Canada) with silk 4-0 ligatures. Muscles were stimulated via field electrodes with supra maximal voltage and isometric (fixed) length was adjusted to yield maximal developed tension. It was found that the small size of the FDB (6-8 mm length, 2-4 mg weight) prevented the hypoxia observed in larger muscles and allowed stable force measurement for 6-8 hours. Muscles were stimulated every 10 minutes with 7 stimuli in succession from 5-100 Hz (1 ms square wave pulses, 350 ms duration) and compounds were infused in to the incubating buffer at 1-10 µM in DMSO (final DMSO concentration 0.1%). Live fiber data is shown for one skeletal muscle activator (FIG. 3). As in skinned fibers, it was observed incremental increases in sub-maximal force without increases in maximal (tetanic) tension. Washout of compound caused a rapid decrease in augmented force to baseline levels within 30 minutes (data not shown).

Example 10

Activation of Skeletal Muscle Fibers

This experiment investigated whether the skeletal muscle activators increased force in-vivo using an in-situ muscle analysis setup in the rat. This technique measures force development in skeletal muscles that still have intact blood and nervous connections, allowing measurement of muscle force in its native environment. For these experiments, the extensor digitorum longus (EDL) muscle, which is present in the hindlimb and has a predominantly fast fiber composition, was utilized. While under isoflurane anesthesia, the distal tendon to this muscle (at the ankle) was exposed with a small incision, then cut and attached to a force transducer (Aurora Scientific, Ontario, Canada). The knee was then clamped with a pin to prevent movement and fix the length of the muscle. The peroneal nerve running to the muscle was exposed at the groin and attached to a pair of platinum hook electrodes. Contraction of the muscle was elicited through stimulation of the nerve through the electrodes at supra maximal voltage. Length of the muscle was adjusted to yield maximal developed tension after a single sub-maximal stimulus (1 ms square wave, 350 ms duration, 30 Hz frequency. Muscle force was then measured at a single sub-tetanic frequency (30 Hz) every 2 minutes. Once force had stabilized, a skeletal muscle activator was administered via the femoral artery at the abdomen as 4 accumulative doses from 2 to 10 mg/kg (given as a 2 minute bolus of 5 mg/ml compound in a 50% PEG300/10% EtOH/40% cavitron formulation).

Figure 4A:
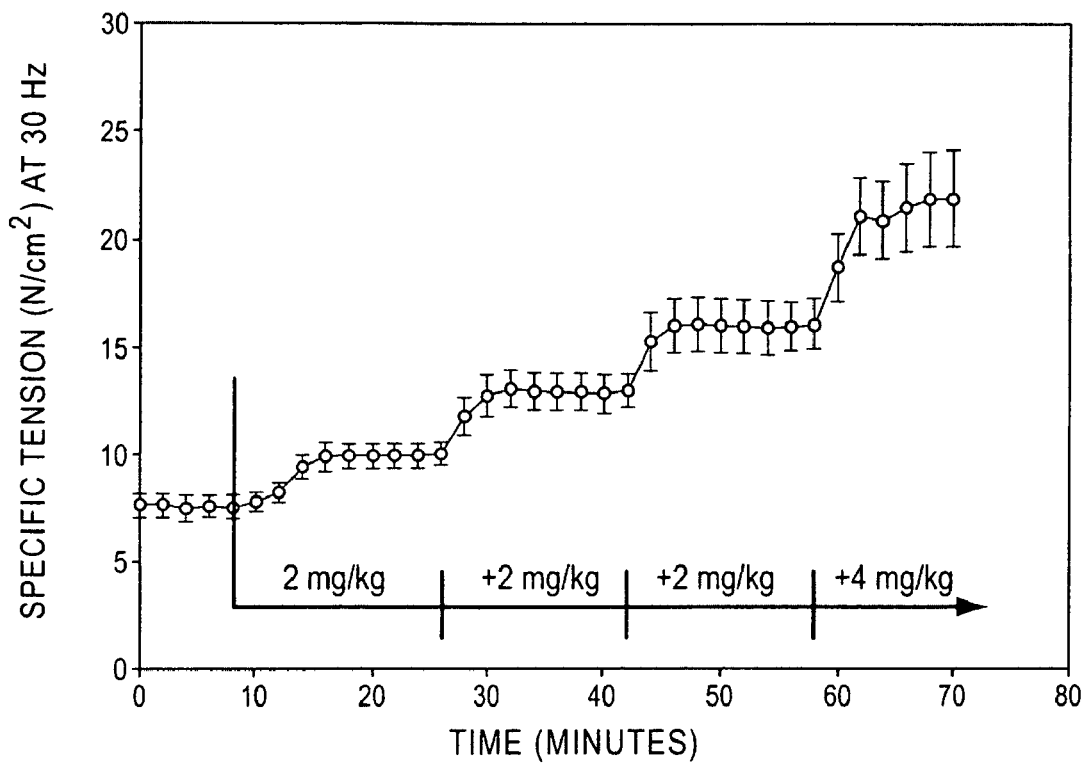
FIG. 4. In-situ response to arterial administration of a skeletal muscle activator.
Figure 4B:
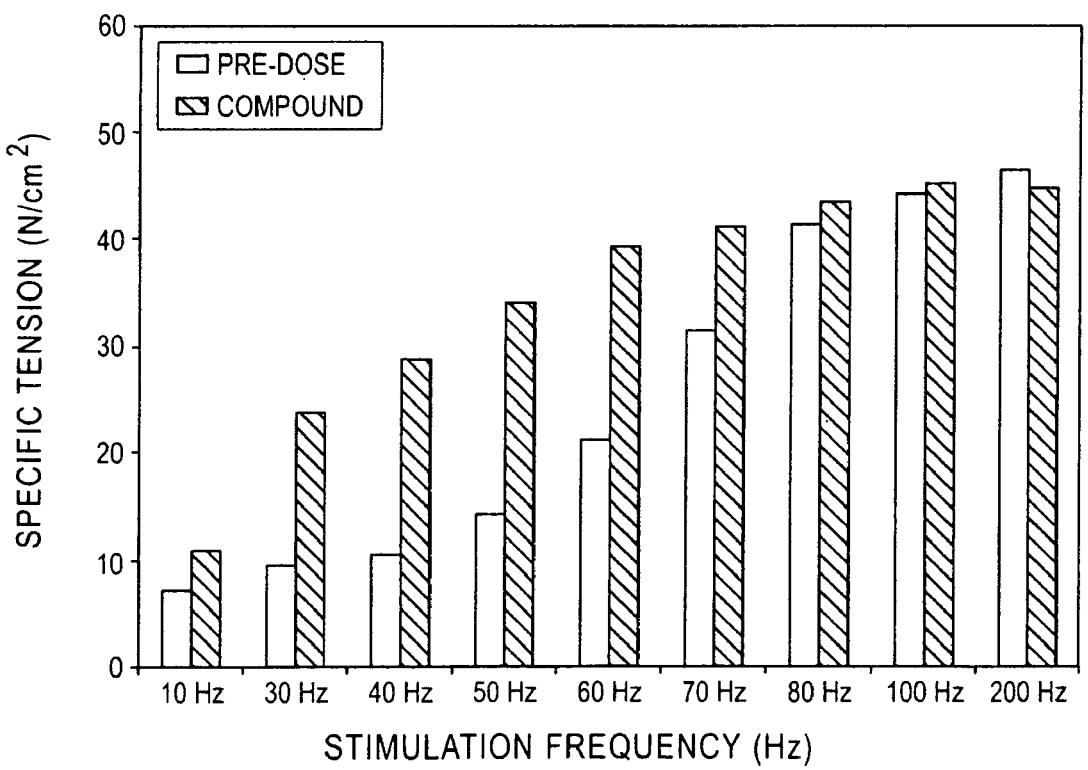

Administration of skeletal muscle activator resulted in a rapid, dose dependent increase in sub-tetanic force without altering maximal force generation (FIG. 4). In separate experiments, blood pressure and heart rate were measured after a 10 mg/kg bolus dose of skeletal muscle activator. No significant change in these metrics was observed, suggesting that the observed effects of the EDL were specific to skeletal muscle (data not shown)

Example 11

Activation of Skeletal Muscle Fibers

Figure 5:
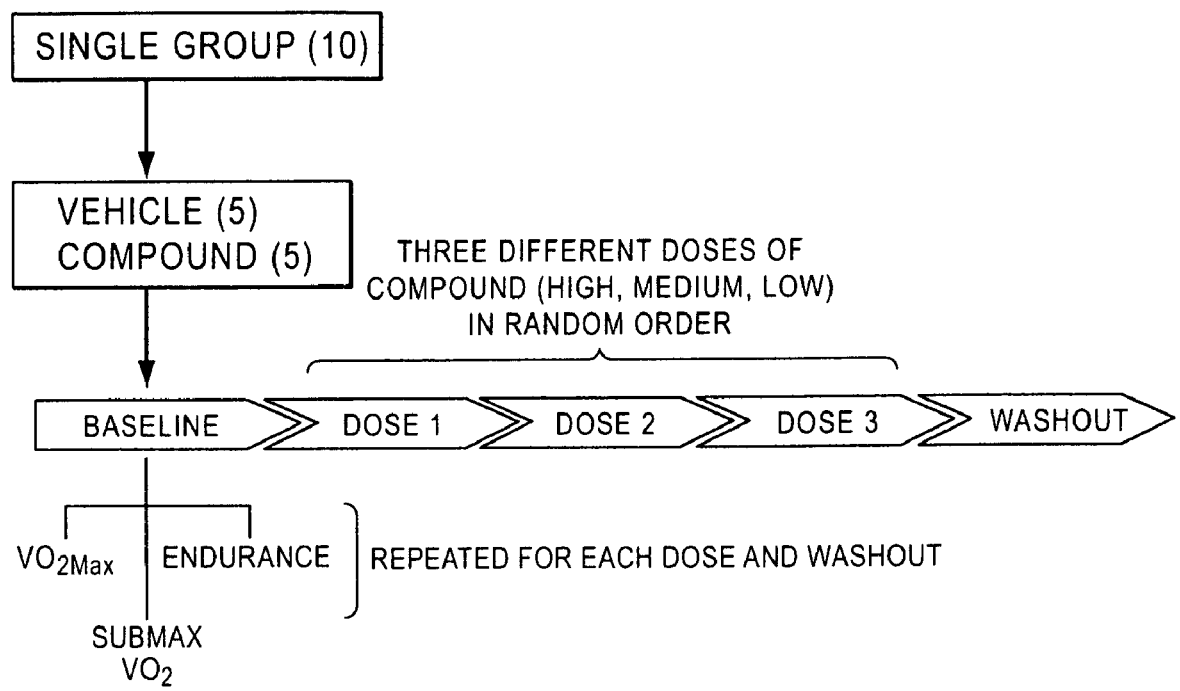
FIG. 5. Study design for treadmill running with healthy rats.

The data described herein show that the skeletal muscle activators have a consistent phenotype on muscle from skinned fibers in-vitro to live muscle in-situ, increasing sub-tetanic force for a given amount of calcium exposure or stimulation. To test whether, in functional assays, this can translate into increases in physical performance, a treadmill running endurance in healthy rats assay is used. See, FIG. 5.

The data provided in the examples show that the skeletal muscle activators disclosed herein have an apparent affinity for the troponin complex in skeletal muscle, and act to sensitize muscle fibers to calcium (for skinned fibers) or depolarizing stimulation (for live muscle). In a non-invasive assay that measures physical function, this appears to translate into increased muscle endurance and efficiency with healthy rats.

Example 12

SOD1(G93A) Mouse Assay

The accepted animal model for ALS is currently the SOD1 (G93A) mouse (Gurney et al., 1994). This transgenic mouse has been engineered to express a mutated form of the Human Cu/Zn superoxide dismutase gene, SOD1. Approximately 10% of classical ALS is familial and among the familial cases, approximately 20% are caused by dominantly inherited mutations in SOD1. Research has shown that these mice develop progressive limb and body weakness around 80 days of age culminating in full limb paralysis, morbidity and death at around 135-140 days. The reason for this decline is progressive death of motor neurons controlling the limbs and diaphragm although the specific cause of death is not well understood. Many of the histological features of disease in the SOD1(G93A) mice are similar to those observed in ALS patients with the main area of disparity appearing to be the degree of compensation observed in the mice through motor unit enlargement and sprouting to denervated muscles. The only approved medication for ALS patients to date, the glutamate antagonist riluzole, also extends lifespan in the SOD1(G93A) mouse suggesting a similar underlying etiology. Another beneficial aspect of this model is that it is readily available from Jackson Laboratories (Bar Harbor, Me.).

Two experimental measures of skeletal muscle activator efficacy using the SOD1(G93A) mouse model:

(i) Acute measurement of muscle force changes during disease progression in normal and SOD1(G93A) mice.

Activity of fast and slow skeletal muscle activators can be confirmed by repeating in-situ muscle analysis of the EDL after acute arterial administration. To measure mouse muscle force, the in-situ analysis setup is adapted with an alternate limb brace and more sensitive force transducer (Aurora Scientific). Pilot experiments performed with the SOD1(G93A) background strain, B6SJL (Jax 100012), have demonstrated the comparable activity of a skeletal muscle activator (FIG. 6).

Figure 6A:
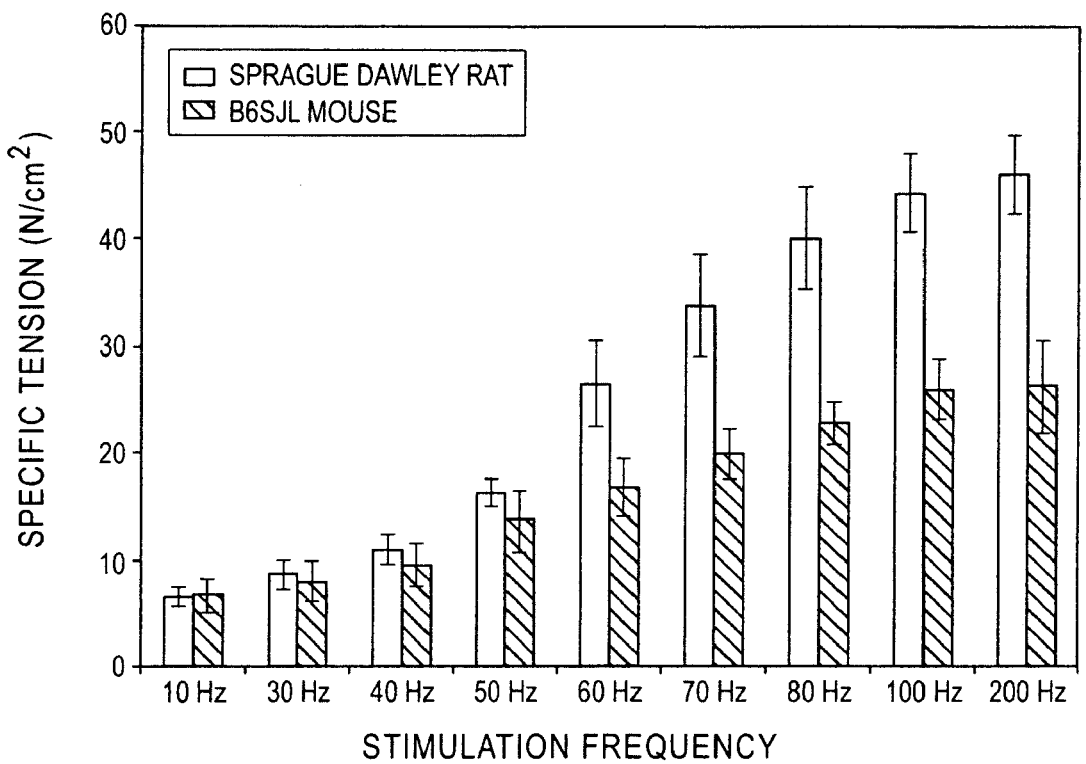
FIGS. 6A and 6B. In-situ EDL response to a skeletal muscle activator after arterial administration in rats and mice.
Figure 6B:
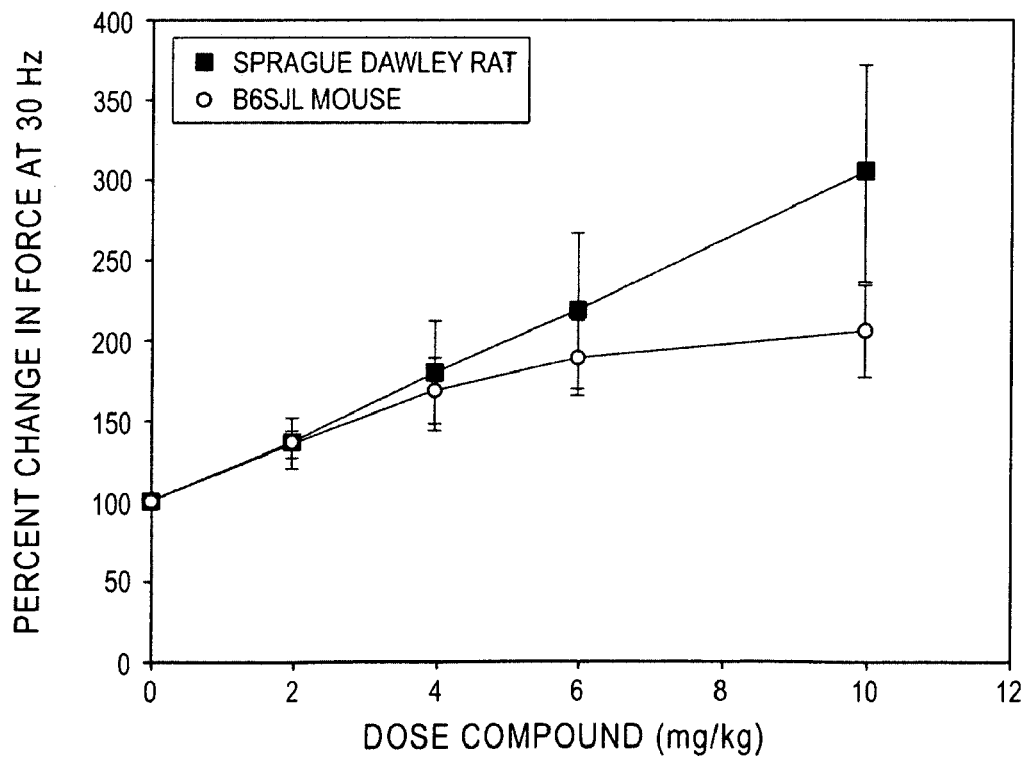

FIG. 6A shows the baseline force frequency relationship in the EDL of rat (n=5) vs mouse (n=9), normalized by cross-sectional area to $N/cm^2$. FIG. 6B shows peak response, expressed as a percent of the baseline force at 30 Hz vs arterial dose of a skeletal muscle activator. Doses were given in an escalating fashion as a 2 minute bolus (5 ml/kg) via the femoral artery and force response at 30 Hz (1 ms stimuli, 350 ms duration) recorded every 2 minutes.

Acute responses to skeletal muscle activator or any other fast or slow activator compound is assessed in the SOD1 (G93A) mice at two stages of disease (onset, day 80 and mid-late stage disease, day 100-110). These assays confirm muscle activity of the compounds in SOD1(G93A) mice and assess how the stage of disease alters responses to fast and slow muscle activators. It has been documented that this mouse model exhibits preferential loss of fast motor neurons. Whether slow skeletal muscle activators have enhanced activity in this model is assessed.

(ii) Effect of chronic exposure of skeletal muscle activators on morbidity, strength and muscle size in SOD1(G93A) mice.

Whether chronic exposure to fast or slow skeletal muscle activators alters the time course of weakness and morbidity SOD1(G93A) mice is assessed. SOD1(G93A) mice are housed until the visible onset of symptoms, shaking and weakness of the hind limbs with handling, around 80 days of age. At this point, mice (3 groups of 30 per compound) are dosed daily by oral gavage with either vehicle (1% HPMC with 0.1% tween-80) or two different dose levels of candidate slow or fast activator compounds. Mice are monitored daily for signs of morbidity (unable to perform the righting response) and weekly to assess limb strength. This is performed with a grip strength meter (Chatillon, Ametek Inc., Largo, Fla.). Mice naturally grip a small bar fixed to a force transducer and are pulled away from the bar by their proximal tail. The peak force from 3 trials each from hindlimb and forelimb will be recorded when the animal releases its grip. Small numbers of animals from each group (e.g., n=5) are removed from each group at two points in the study, after onset of disease (~100 days) and at the mid/late-stage of the disease (~115 days). Animals in these groups are euthanized and select muscles are isolated (Triceps, Pectoralis, Quadriceps, Gastroc/Soleus) and their weight recorded. Histology is performed on Triceps and Quadriceps and fiber diameter quantified.

While certain embodiments have been shown and described, various modifications and substitutions may be made thereto without departing from the spirit and scope of the invention. Accordingly, it is to be understood that the present invention has been described by way of illustration and not limitations.

What is claimed is:

1. A method for increasing time to fast skeletal muscle fiber fatigue, the method comprising:
    selectively binding troponin C in the troponin complex of the fast skeletal muscle fiber; and
    allowing said fast skeletal muscle fiber to respond with enhanced force or increased time to fatigue as compared to a fast skeletal muscle fiber having at least some troponin C which is not selectively bound,
wherein the troponin C is bound with a compound of Formula I or Formula II:

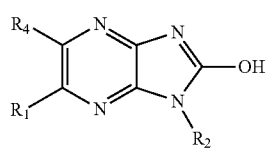

Formula I

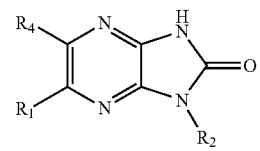

Formula II or a pharmaceutically acceptable salt thereof, wherein
    $R_1$ is selected from alkenyl and alkynyl;
    $R_4$ is hydrogen; and
    $R_2$ is selected from 3-pentyl, 4-heptyl, 4-methyl-1-morpholinopentan-2-yl, isobutyl, cyclohexyl, cyclopropyl, sec-butyl, tert-butyl, isopropyl, 1-hydroxybutan-2-yl, tetrahydro-2H-pyran-4-yl, 1-methoxybutan-2-yl, 1-aminobutan-2-yl, and 1-morpholinobutan-2-yl;
    provided that $R_1$ is not hex-1-enyl; and
    allowing said fast skeletal muscle fiber to respond with enhanced force or increased time to fatigue as compared to a fast skeletal muscle fiber having at least some troponin C which is not selectively bound.

2. The method of claim 1, wherein $R_1$ is selected from isobuten-1-yl, (Z)-propen-1-yl, (E)-propen-1-yl, propen-2-yl, vinyl, and ethynyl.

3. The method of claim 2, wherein $R_1$ is ethynyl.

4. The method of claim 2, wherein $R_2$ is selected from 3-pentyl, 4-heptyl, isobutyl, sec-butyl, tert-butyl and isopropyl.

5. The method of claim 1, wherein the compound is selected from:
    1-[(1R)-1-(morpholin-4-ylmethyl)propyl]-6-ethynylimidazo[4,5-b]pyrazin-2-ol;
    1-(pentan-3-yl)-6-(prop-1-ynyl)-1H-imidazo[4,5-b]pyrazin-2-ol; and
    6-ethynyl-1-(pentan-3-yl)-1H-imidazo[4,5-b]pyrazin-2-ol;
or a pharmaceutically acceptable salt thereof.

6. The method of claim 1, wherein the compound is selected from:
    (E)-1-(pentan-3-yl)-6-(prop-1-enyl)-1H-imidazo[4,5-b]pyrazin-2-ol;
    (E)-1-cyclohexyl-6-(prop-1-enyl)-1H-imidazo[4,5-b]pyrazin-2-ol;
    (E)-1-cyclopropyl-6-(prop-1-enyl)-1H-imidazo[4,5-b]pyrazin-2-ol;
    (E)-1-isopropyl-6-(prop-1-enyl)-1H-imidazo[4,5-b]pyrazin-2-ol;
    (E)-6-(prop-1-enyl)-1-(tetrahydro-2H-pyran-4-yl)-1H-imidazo[4,5-b]pyrazin-2-ol;
    (Z)-1-(pentan-3-yl)-6-(prop-1-enyl)-1H-imidazo[4,5-b]pyrazin-2-ol;
    (Z)-1-cyclohexyl-6-(prop-1-enyl)-1H-imidazo[4,5-b]pyrazin-2-ol;
    (Z)-1-cyclopropyl-6-(prop-1-enyl)-1H-imidazo[4,5-b]pyrazin-2-ol;
    (Z)-1-isopropyl-6-(prop-1-enyl)-1H-imidazo[4,5-b]pyrazin-2-ol;
    (Z)-6-(prop-1-enyl)-1-(tetrahydro-2H-pyran-4-yl)-1H-imidazo[4,5-b]pyrazin-2-ol;
    1-(ethylpropyl)-6-vinylimidazo[4,5-b]pyrazin-2-ol; and
    1-(ethylpropyl)-6-(1-methylvinyl)imidazo[4,5-b]pyrazin-2-ol;
or a pharmaceutically acceptable salt thereof.

7. The method of claim 1, wherein the compound is selected from:
- (R)-6-ethynyl-1-(1-morpholinobutan-2-yl)-1H-imidazo[4,5-b]pyrazin-2(3H)-one;
- 1-(pentan-3-yl)-6-(prop-1-ynyl)-1H-imidazo[4,5-b]pyrazin-2(3H)-one; and
- 6-ethynyl-1-(pentan-3-yl)-1H-imidazo[4,5-b]pyrazin-2(3H)-one;

or a pharmaceutically acceptable salt thereof.

8. The method of claim 1, wherein the compound is selected from:
- (E)-1-(pentan-3-yl)-6-(prop-1-enyl)-1H-imidazo[4,5-b]pyrazin-2(3H)-one;
- (E)-1-cyclohexyl-6-(prop-1-enyl)-1H-imidazo[4,5-b]pyrazin-2(3H)-one;
- (E)-1-cyclopropyl-6-(prop-1-enyl)-1H-imidazo[4,5-b]pyrazin-2(3H)-one;
- (E)-1-isopropyl-6-(prop-1-enyl)-1H-imidazo[4,5-b]pyrazin-2(3H)-one;
- (E)-6-(prop-1-enyl)-1-(tetrahydro-2H-pyran-4-yl)-1H-imidazo[4,5-b]pyrazin-2(3H)-one;
- (Z)-1-(pentan-3-yl)-6-(prop-1-enyl)-1H-imidazo[4,5-b]pyrazin-2(3H)-one;
- (Z)-1-cyclohexyl-6-(prop-1-enyl)-1H-imidazo[4,5-b]pyrazin-2(3H)-one;
- (Z)-1-cyclopropyl-6-(prop-1-enyl)-1H-imidazo[4,5-b]pyrazin-2(3H)-one;
- (Z)-1-isopropyl-6-(prop-1-enyl)-1H-imidazo[4,5-b]pyrazin-2(3H)-one;
- (Z)-6-(prop-1-enyl)-1-(tetrahydro-2H-pyran-4-yl)-1H-imidazo[4,5-b]pyrazin-2(3H)-one;
- 1-(pentan-3-yl)-6-vinyl-1H-imidazo[4,5-b]pyrazin-2(3H)-one; and
- 1-(pentan-3-yl)-6-(prop-1-en-2-yl)-1H-imidazo[4,5-b]pyrazin-2(3H)-one;

or a pharmaceutically acceptable salt thereof.

9. The method of claim 1, wherein the sensitivity of the fast skeletal muscle fiber to calcium ion is increased.

10. The method of claim 1, wherein the fast skeletal muscle fiber responds with enhanced force as compared to a fast skeletal muscle fiber having at least some troponin C which is not selectively bound.

11. The method of claim 1, wherein fast skeletal muscle fiber responds with increased time to fatigue as compared to a fast skeletal muscle fiber having at least some troponin C which is not selectively bound.

12. A method for increasing time to skeletal muscle fatigue, the method comprising:
- selectively binding troponin C in the troponin complex of the sarcomere of a fast skeletal muscle fiber of the skeletal muscle at a first calcium ion concentration to form a bound complex; and
- activating said fast skeletal muscle fiber with said bound complex, whereby said fast skeletal muscle fiber responds with enhanced force or increased time to fatigue as compared to a fast skeletal muscle fiber exposed to said first calcium ion concentration but not comprising said bound complex, wherein the troponin C is bound with a compound of Formula I or Formula II:

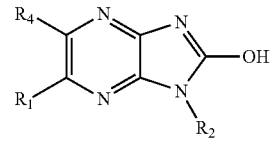

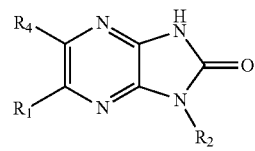

or a pharmaceutically acceptable salt thereof, wherein
- $R_1$ is selected from alkenyl and alkynyl;
- $R_4$ is hydrogen; and
- $R_2$ is selected from 3-pentyl, 4-heptyl, 4-methyl-1-morpholinopentan-2-yl, isobutyl, cyclohexyl, cyclopropyl, sec-butyl, tert-butyl, isopropyl, 1-hydroxybutan-2-yl, tetrahydro-2H-pyran-4-yl, 1-methoxybutan-2-yl, 1-aminobutan-2-yl, and 1-morpholinobutan-2-yl;
provided that $R_1$ is not hex-1-enyl.

13. The method of claim 12, wherein $R_1$ is selected from isobuten-1-yl, (Z)-propen-1-yl, (E)-propen-1-yl, propen-2-yl, vinyl, and ethynyl.

14. The method of claim 13, wherein $R_1$ is ethynyl.

15. The method of claim 13, wherein $R_2$ is selected from 3-pentyl, 4-heptyl, isobutyl, sec-butyl, tert-butyl and isopropyl.

16. The method of claim 12, wherein the compound is selected from:
- 1-[(1R)-1-(morpholin-4-ylmethyl)propyl]-6-ethynylimidazo[4,5-b]pyrazin-2-ol;
- 1-(pentan-3-yl)-6-(prop-1-ynyl)-1H-imidazo[4,5-b]pyrazin-2-ol; and
- 6-ethynyl-1-(pentan-3-yl)-1H-imidazo[4,5-b]pyrazin-2-ol;

or a pharmaceutically acceptable salt thereof.

17. The method of claim 12, wherein the compound is selected from:
- (E)-1-(pentan-3-yl)-6-(prop-1-enyl)-1H-imidazo[4,5-b]pyrazin-2-ol;
- (E)-1-cyclohexyl-6-(prop-1-enyl)-1H-imidazo[4,5-b]pyrazin-2-ol;
- (E)-1-cyclopropyl-6-(prop-1-enyl)-1H-imidazo[4,5-b]pyrazin-2-ol,
- (E)-1-isopropyl-6-(prop-1-enyl)-1H-imidazo[4,5-b]pyrazin-2-ol;
- (E)-6-(prop-1-enyl)-1-(tetrahydro-2H-pyran-4-yl)-1H-imidazo[4,5-b]pyrazin-2-ol;
- (Z)-1-(pentan-3-yl)-6-(prop-1-enyl)-1H-imidazo[4,5-b]pyrazin-2-ol;
- (Z)-1-cyclohexyl-6-(prop-1-enyl)-1H-imidazo[4,5-b]pyrazin-2-ol;
- (Z)-1-cyclopropyl-6-(prop-1-enyl)-1H-imidazo[4,5-b]pyrazin-2-ol;
- (Z)-1-isopropyl-6-(prop-1-enyl)-1H-imidazo[4,5-b]pyrazin-2-ol;
- (Z)-6-(prop-1-enyl)-1-(tetrahydro-2H-pyran-4-yl)-1H-imidazo[4,5-b]pyrazin-2-ol;

1-(ethylpropyl)-6-vinylimidazo[4,5-b]pyrazin-2-ol; and
1-(ethylpropyl)-6-(1-methylvinyl)imidazo[4,5-b]pyrazin-2-ol;

or a pharmaceutically acceptable salt thereof.

18. The method of claim 12, wherein the compound is selected from:
(R)-6-ethynyl-1-(1-morpholinobutan-2-yl)-1H-imidazo[4,5-b]pyrazin-2(3H)-one;
1-(pentan-3-yl)-6-(prop-1-ynyl)-1H-imidazo[4,5-b]pyrazin-2(3H)-one; and
6-ethynyl-1-(pentan-3-yl)-1H-imidazo[4,5-b]pyrazin-2(3H)-one;

or a pharmaceutically acceptable salt thereof.

19. The method of claim 12, wherein the compound is selected from:
(E)-1-(pentan-3-yl)-6-(prop-1-enyl)-1H-imidazo[4,5-b]pyrazin-2(3H)-one;
(E)-1-cyclohexyl-6-(prop-1-enyl)-1H-imidazo[4,5-b]pyrazin-2(3H)-one;
(E)-1-cyclopropyl-6-(prop-1-enyl)-1H-imidazo[4,5-b]pyrazin-2(3H)-one;
(E)-1-isopropyl-6-(prop-1-enyl)-1H-imidazo[4,5-b]pyrazin-2(3H)-one;
(E)-6-(prop-1-enyl)-1-(tetrahydro-2H-pyran-4-yl)-1H-imidazo[4,5-b]pyrazin-2(3H)-one;
(Z)-1-(pentan-3-yl)-6-(prop-1-enyl)-1H-imidazo[4,5-b]pyrazin-2(3H)-one;
(Z)-1-cyclohexyl-6-(prop-1-enyl)-1H-imidazo[4,5-b]pyrazin-2(3H)-one;
(Z)-1-cyclopropyl-6-(prop-1-enyl)-1H-imidazo[4,5-b]pyrazin-2(3H)-one;
(Z)-1-isopropyl-6-(prop-1-enyl)-1H-imidazo[4,5-b]pyrazin-2(3H)-one;
(Z)-6-(prop-1-enyl)-1-(tetrahydro-2H-pyran-4-yl)-1H-imidazo[4,5-b]pyrazin-2(3H)-one;
1-(pentan-3-yl)-6-vinyl-1H-imidazo[4,5-b]pyrazin-2(3H)-one; and
1-(pentan-3-yl)-6-(prop-1-en-2-yl)-1H-imidazo[4,5-b]pyrazin-2(3H)-one;

or a pharmaceutically acceptable salt thereof.

20. The method of claim 12, wherein the fast skeletal muscle fiber responds with enhanced force as compared to a fast skeletal muscle fiber exposed to said first calcium ion concentration but not comprising said bound complex.

21. The method of claim 12, wherein fast skeletal muscle fiber responds with increased time to fatigue as compared to a fast skeletal muscle fiber exposed to said first calcium ion concentration but not comprising said bound complex.

* * * * *